(12) United States Patent
Ross et al.

(10) Patent No.: US 12,570,956 B2
(45) Date of Patent: Mar. 10, 2026

(54) EFFICIENT DERIVATION OF STABLE PLURIPOTENT BOVINE EMBRYONIC STEM CELLS

(71) Applicants: The Regents of the University of California, Oakland, CA (US); Salk Institute for Biological Science, La Jolla, CA (US)

(72) Inventors: Pablo Juan Ross, Davis, CA (US); Yanina Bogliotti, Davis, CA (US); Marcela Vilarino, Davis, CA (US); Juan Carlos Izpisua Belmonte, La Jolla, CA (US); Jun Wu, La Jolla, CA (US)

(73) Assignees: The Regents of the University of California, Oakland, CA (US); Salk Institute for Biological Studies, La Jolla, CA (US)

( * ) Notice: Subject to any disclaimer, the term of this patent is extended or adjusted under 35 U.S.C. 154(b) by 887 days.

(21) Appl. No.: 16/960,812

(22) PCT Filed: Jan. 11, 2019

(86) PCT No.: PCT/US2019/013299
§ 371 (c)(1),
(2) Date: Jul. 8, 2020

(87) PCT Pub. No.: WO2019/140260
PCT Pub. Date: Jul. 18, 2019

(65) Prior Publication Data
US 2020/0385674 A1 Dec. 10, 2020

Related U.S. Application Data

(60) Provisional application No. 62/616,975, filed on Jan. 12, 2018.

(51) Int. Cl.
| | |
|---|---|
| *C12N 5/0735* | (2010.01) |
| *A01K 67/0275* | (2024.01) |
| *C12N 5/075* | (2010.01) |
| *C12N 5/076* | (2010.01) |
| *C12N 15/01* | (2006.01) |
| *C12N 15/877* | (2010.01) |

(52) U.S. Cl.
CPC ........ *C12N 5/0606* (2013.01); *A01K 67/0275* (2013.01); *C12N 5/0609* (2013.01); *C12N 5/061* (2013.01); *C12N 15/01* (2013.01); *C12N 15/8771* (2013.01); *A01K 2207/12* (2013.01); *A01K 2217/05* (2013.01); *C12N 2501/115* (2013.01); *C12N 2501/15* (2013.01); *C12N 2501/415* (2013.01); *C12N 2506/04* (2013.01)

(58) Field of Classification Search
CPC .............. C12N 5/0606; C12N 15/8771; C12N 2501/115; C12N 2501/15; C12N 2501/415
See application file for complete search history.

(56) References Cited

U.S. PATENT DOCUMENTS

| | | | |
|---|---|---|---|
| 5,523,226 | A | 6/1996 | Wheeler |
| 6,436,701 | B1 | 8/2002 | Evans et al. |
| 6,545,199 | B1 | 4/2003 | Anderson et al. |
| 7,071,373 | B1 | 7/2006 | Wheeler |
| 2012/0167242 | A1 | 6/2012 | Wiles et al. |
| 2013/0273649 | A1 | 10/2013 | Wu et al. |
| 2016/0360736 | A1 | 12/2016 | Koentgen |

FOREIGN PATENT DOCUMENTS

| | | |
|---|---|---|
| CN | 101914487 | 12/2010 |
| WO | WO-95/16770 A1 | 6/1995 |
| WO | WO-2017/025061 A1 | 2/2017 |

OTHER PUBLICATIONS

Bogliotti et al (Bovine Embryonic Stem-Like Cells Derived From in Vitro-Produced Blastocysts. Reproduction, Fertility and Development, vol. 29, Dec. 2016) (Year: 2016).*
Liu et al (A novel chemical-defined medium with bFGF and N2B27 supplements supports undifferentiated growth in human embryonic stem cells. Biochemical and Biophysical Research Communications, vol. 346, 2006). (Year: 2006).*
Saidova (Bovine stem cells: methodology and applications, SOJ Vet Sci, vol. 5, Jan. 4, 2019 (Year: 2019).*
Sato et al (Simplification of culture conditions and feeder-free expansion of bovine embryonic stem cells. Scientific Reports, vol. 11, 2021 (Year: 2021).*
Burke et al (Stem Cell-Derived Exosomes: A Potential Alternative Therapeutic Agent in Orthopaedics. Stem Cells International, vol. 2016 (Year: 2016).*
Munoz et al (Embryonic Stem Cells in Cattle. Reprod Dom Anim, vol. 43, 2008) (Year: 2008).*
DMEM/F12 and Neurobasal Media Formulations (Year: 2023).*
Bogliotti (Bovine Embryonic Stem-Like Cells Derived From in Vitro-Produced Blastocysts. Reproduction, Fertility and Development, vol. 29, Dec. 2016; cited in IDS dated Dec. 14, 2021 (Year: 2016).*
Yao et al (Long-term self-renewal and directed differentiation of human embryonic stem cells in chemically defined conditions, PNAS, vol. 103, 2006 (Year: 2006).*
Wu et al (An alternative pluripotent state confers interspecies chimaeric competency. Nature | vol. 521 | May 21, 2015). (Year: 2015).*

(Continued)

*Primary Examiner* — Emily A Cordas
*Assistant Examiner* — Matasha Dhar
(74) *Attorney, Agent, or Firm* — Foley & Lardner LLP

(57) ABSTRACT
This disclosure provides ungulate embryonic stem cells (ESCs) derived from the inner cell mass of pre-implantation blastocysts or pluripotent cells from embryos. From an agricultural and biomedical perspectives, the derivation of stable ESCs from domestic ungulates is important for genomic testing and selection, genetic engineering, and providing an experimental tool for studying human diseases. Cattle are one of the most important domestic ungulates that are commonly used for food and bioreactors.

9 Claims, 20 Drawing Sheets

(56)                  References Cited

OTHER PUBLICATIONS

Yue et al (Biology of the Extracellular Matrix: An Overview. J Glaucoma. 2014 ; : S20-S23) (Year: 2014).*

Hughes et al (Matrigel: A complex protein mixture required for optimal growth of cell culture. Proteomics 2010, 10, 1886-1890 (Year: 2010).*

Catalog# 5051, Sigma Aldrich (Year: 2024).*

Soto et al (Simplification of culture conditions and feeder-free expansion of bovine embryonic stem cells. Scientific Reports, 11:11045, May 26, 2021 (Year: 2021).*

Beattie et al (Activin A Maintains Pluripotency of Human Embryonic Stem Cells in the Absence of Feeder Layers. Stem Cells 2005; 23:489-495 (Year: 2005).*

Kishimoto et al (Establishment of novel common marmoset embryonic stem cell lines under various conditions. Stem Cell Research 53 (2021) 102252 (Year: 2021).*

Yuan et al (Capturing Bovine Pluripotency, PNAS, 115(9): 1962-63 (2018 (Year: 2018).*

International Search Report dated Apr. 8, 2019, from application No. PCT/US2019/013299.

Office Action on CN 201980007033.X DTD Nov. 2, 2022, 8 pages (including English translation).

Bogliotti et al. "Bovine Embryonic Stem-Like Cells Derived from In Vitro-Produced Blastocysts", Reproduction Fertility and Development, vol. 29, No. 1, p. 108 (2017).

Bogliotti et al. "Efficient derivation of stable primed pluripotent embryonic stem cells from bovine blastocysts", Proceedings of the National Academy of Sciences, vol. 115, No. 9, pp. 2090-2095 (2018).

Bogliotti et al. "Transcriptional and Epigenetic Regulation of Bovine Pluripotency", Dissertation, University of California, Davis, pp. 1-230 (2017).

Foreign Search Report on EP 19739101.4 DTD Sep. 14, 2021.

Wu et al., "An alternative pluripotent state confers interspecies chimaeric competency", Nature, 521:316-321 (2015).

Office Action on IL Application No. 275568 DTD Jan. 8, 2024, 4 pages.

"2 Bovine Embryonic Stem-Like Cells Derived From in Vitro-Produced Blastocysts", Bogliotti et al., Reproduction Fertility and Development, vol. 29, Issue 1, p. 108-109, published Dec. 2, 2016.

Anderson, et al., "Development of bovine and porcine embryonic teratomas in athymic mice", Animal Reproduction Science 45 (1996) 231-240.

Cao, et al., Isolation and culture of bovine embryonic stem cells. Methods in Molecular Biology 1074, 111-123 (2013).

Cao, et al., "Isolation and culture of primary bovine embryonic stem cell colonies by a novel method", Journal of Experimental Zoology 311, 368-376 (2009).

Cibelli, et al., "Transgenic bovine chimeric offspring produced from somatic cell-derived stem-like cells", Nature Biotechnology 16, 642-646 (1998).

Cong, et al., "Effects of different feeder layers on culture of bovine embryonic stem cell-like cells in vitro", Cytotechnology (2014) 66: 995-1005.

Furusawa, et al., "Characteristics of bovine inner cell mass-derived cell lines and their fate in chimeric conceptuses", Biology of Reproduction (2013) 89(2): 28, 1-12.

Gong, et al., "Culture conditions and enzymatic passaging of bovine ESC-like cells", Cellular Reprogramming 12, 151-160 (2010).

Guastali, et al., "Influence of culture medium and age of bovine blastocysts in established colonies of embryonic stem cells", Journal of Stem Cells, vol. 9, 225-234 (2014).

Iwasaki, et al., "Production of live calves derived from embryonic stem-like cells aggregated with tetraploid embryos" Biology of Reproduction 62, 470-475 (2000).

Jin, et al., "Culture conditions for bovine embryonic stem cell-like cells isolated from blastocysts after external fertilization", Cytotechnology (2012) 64: 379-389.

Kim, et al., "Establishment of bovine embryonic stem cell lines using a minimized feeder cell drop", Cellular Reprogramming 14, 520-529 (2012).

Kim, et al., "Microarray analysis of embryoderived bovine pluripotent cells: the vulnerable state of bovine embryonic stem cells", PLoS One 12, e0173278. doi:10.1371/JOURNAL.PONE.0173278.

Kwon, et al., "Epiblast isolation by a new four stage method (peeling) from whole bovine cloned blastocysts", Cell Biology International 33, (2009) 309-317.

Lim, et al., "A novel, efficient method to derive bovine and mouse embryonic stem cells with in vivo differentiation potential by treatment with 5-azacytidine", Theriogenology 76 (2011) 133-142.

Madeja, et al., "WNT/b-catenin signaling affects cell lineage and pluripotency-specific gene expression in bovine blastocysts: prospects for bovine embryonic stem cell derivation", Stem Cells and Development, vol. 24, No. 20, 2015.

Maruotti, et al., "Efficient derivation of bovine embryonic stem cells needs more than active core pluripotency factors", Molecular Reproduction & Development, 79: 461-477 (2012).

Mitalipova, et al., "Pluripotency of bovine embryonic cell line derived from precompacting embryos", Cloning 3, 59-67 (2001).

Munoz, et al., "Conventional pluripotency markers are unspecific for bovine embryonic-derived cell-lines", Theriogenology 69, (2008) 1159-1164.

Ozawa, et al., "Importance of culture conditions during the morula-to-blastocyst period on capacity of inner cell-mass cells of bovine blastocysts for establishment of self-renewing pluripotent cells", Theriogenology 78, (2012) 1243-1251.

Pant, et al., "Expression of pluripotency-related genes during bovine inner cell mass explant culture", Cloning and Stem Cells 11,355-365 (2008).

Park, et al., "Thiazovivin, a Rho kinase inhibitor, improves stemness maintenance of embryo-derived stem-like cells under chemically defined culture conditions in cattle", Animal Reproduction Science 161 (2015) 47-57 doi:10.1016/J.ANIREPROSCI.2015.08.003.

Pashaiasl, et al., "Cryopreservation and long-term maintenance of bovine embryo-derived cell lines", Reproduction, Fertility and Development, 2013, 25, 707-718.

Pashaiasl, et al., "The efficient generation of cell lines from bovine parthenotes", Cellular Reprogramming 12, 571-579 (2010).

Polejaeva, et al., Isolation and Long-Term Culture of Mink and Bovine Embryonic Stem-Like Cells, (1995). Theriogenology 43, 300. [Abstract].

Roach, et al., "Bovine embryonic stem cells", Methods in Enzymology 418, 21-37 (2006).

Saito, et al., "Bovine embryonic stem cell-like cell lines cultured over several passages" Roux's Arch Dev Biol (1992) 201: 134-141.

Saito, et al., "Generation of cloned calves and transgenic chimeric embryos from bovine embryonic stem-like cells", Biochemical and Biophysical Research Communications 309, (2003) 104-113.

Stice, et al., Pluripotent bovine embryonic cell lines direct embryonic development following nuclear transfer. Biology of Reproduction 54, 100-110 (1996).

Talbot, et al., In vitro pluripotency of epiblasts derived from bovine blastocysts. Molecular Reproduction and Development, 42:35-52 (1995).

Van Stekelenbugh-Hamers, et al., "Isolation and Characterization of Permanent Cell Lines from inner Cell Mass Cells of Bovine Blastocysts", Molecular Reproduction and Development 40: 444-454 (1995).

Van Stekelenbugh-Hamers, A. E. P. (1995). Isolation and characterization of permanent cell lines from inner cell mass cells of bovine blastocysts. Mol. Reprod. Dev. 40, 444-454. doi:10.1002/MRD.1080400408.

Verma, et al., "Dual kinase inhibition promotes pluripotency in finite bovine embryonic cell lines", Stem Cells and Development, (2013) 22, 1728-1742.

Wang, et al., "Generation and characterization of pluripotent stem cells from cloned bovine embryos", Biology of Reproduction 73, 149-155 (2005).

(56)         References Cited

OTHER PUBLICATIONS

Wu, et al., "Establishment of bovine embryonic stem cells after knockdown of CDX2", Science Reports 6, 28343. doi:10.1038/ SREP28343.
Yadav, et al., "Bovine ICM derived cells express the Oct4 ortholog", Molecular Reproduction and Development 72: 182-190 (2005).

* cited by examiner

| | Gene | CTFR-bESC | Whole blastocyst | Fibroblast |
|---|---|---|---|---|
| ICM | POU5F1 | 166.95 | 52.25 | 0 |
| | NANOG | 3.35 | 5.75 | 0 |
| | SOX2 | 149.55 | 2.95 | 1.05 |
| | LIN28B | 85.8 | 0.75 | 0 |
| | DNMT3B | 88.05 | 27.25 | 0.25 |
| | UTF1 | 7.15 | 0.15 | 0 |
| | SALL4 | 54.85 | 5.7 | 0 |
| | Gene | CTFR-bESC | Whole blastocyst | Fibroblast |
|---|---|---|---|---|
| TE | CDX2 | 0 | 35.2 | 0 |
| | GATA2 | 0.05 | 4.65 | 2.5 |
| | GATA3 | 0.1 | 14.4 | 0.1 |
| | ELF3 | 0.45 | 1.4 | 0.4 |
| | FGF4 | 0 | 0.55 | 0 |
| | TFAP2A | 0.4 | 0.95 | 16.65 |
| PE | GATA6 | 0.15 | 17.6 | 0 |
| | HNF4A | 0 | 6.45 | 0 |
| | PDGFRA | 1.7 | 10.85 | 57.55 |
FIG. 1C
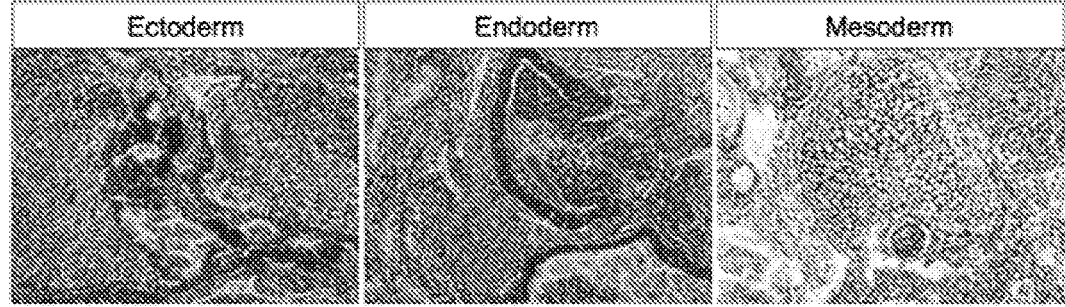
FIG. 1D
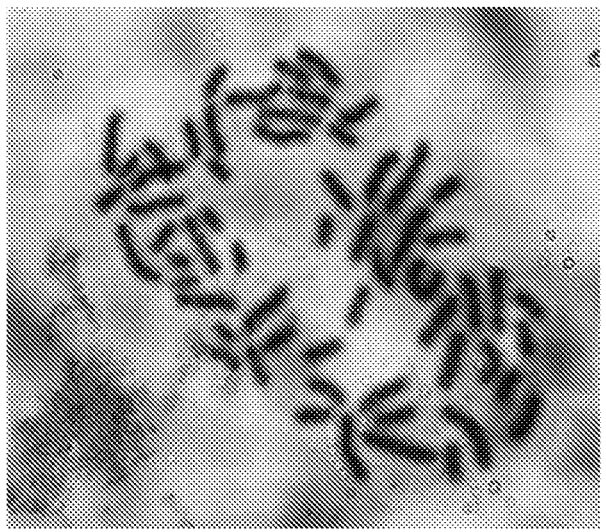
2N=60
FIG. 2A

| | Gene | CTFR-bESC A | | | | CTFR-bESC B | | | | Whole Blastocyst | | Fibroblast | |
|---|---|---|---|---|---|---|---|---|---|---|---|---|---|
| | | p13 | p23 | p35 | p45 | p12 | p24 | p35 | p46 | A | B | A | B |
| ICM | POU5F1 | | | | | | | | | 48.5 | 33.1 | 0.2 | 0.0 |
| | NANOG | 17.2 | 26.3 | 20.1 | 37.0 | 29.2 | 46.1 | 11.2 | 37.1 | 0.6 | 4.4 | 0.0 | 0.0 |
| | SOX2 | 204.6 | 184.1 | 73.6 | 169.0 | 166.0 | 170.0 | 178.7 | 166.9 | 1.9 | 3.1 | 1.9 | 0.2 |
| | LIN28B | 54.6 | 34.8 | 45.2 | 36.4 | 40.3 | 39.2 | 44.7 | 32.6 | 2.0 | 0.3 | 0.0 | 0.0 |
| | DNMT3B | 149.4 | 117.8 | 48.6 | 106.9 | 141.1 | 134.1 | 72.2 | 116.1 | 29.4 | 21.9 | 0.4 | 0.3 |
| | UTF1 | 11.0 | 15.1 | 20.0 | 12.9 | 15.8 | 17.9 | 9.9 | 13.2 | 0.1 | 0.3 | 0.0 | 0.0 |
| | SALL4 | 40.4 | 28.7 | 34.3 | 28.7 | 38.4 | 32.6 | 28.7 | 27.2 | 4.5 | 4.7 | 0.0 | 0.0 |
| TE | CDX2 | 0.0 | 0.0 | 0.0 | 0.0 | 0.0 | 0.0 | 0.0 | 0.0 | 13.3 | 15.7 | 0.0 | 0.0 |
| | GATA2 | 0.2 | 0.3 | 0.2 | 0.3 | 0.2 | 0.3 | 0.2 | 0.3 | 8.8 | 3.4 | 1.4 | 3.5 |
| | GATA3 | 0.2 | 0.4 | 0.1 | 0.2 | 0.3 | 0.5 | 0.6 | 0.4 | 12.6 | 12.9 | 0.0 | 0.2 |
| | ELF3 | 0.7 | 1.4 | 0.5 | 1.6 | 1.1 | 1.5 | 0.8 | 1.5 | 0.1 | 0.1 | 0.3 | 0.4 |
| | FGF4 | 0.0 | 0.0 | 0.0 | 0.1 | 0.0 | 0.0 | 0.0 | 0.0 | 2.2 | 4.1 | 0.0 | 0.0 |
| | TFAP2A | 0.3 | 0.4 | 0.9 | 0.6 | 0.4 | 0.5 | 0.7 | 0.7 | 0.2 | 0.4 | 21.2 | 12.0 |
| PE | GATA6 | 0.3 | 0.7 | 0.4 | 0.4 | 0.4 | 0.4 | 0.7 | 0.5 | 13.5 | 16.5 | 0.0 | 0.0 |
| | HNF4A | 0.2 | 0.0 | 0.1 | 0.1 | 0.0 | 0.1 | 0.1 | 0.0 | 1.7 | 1.6 | 0.0 | 0.0 |
| | PDGFRA | 1.0 | 1.9 | 2.3 | 2.2 | 0.7 | 1.1 | 1.4 | 2.5 | 14.1 | 20.3 | 65.8 | 49.6 |

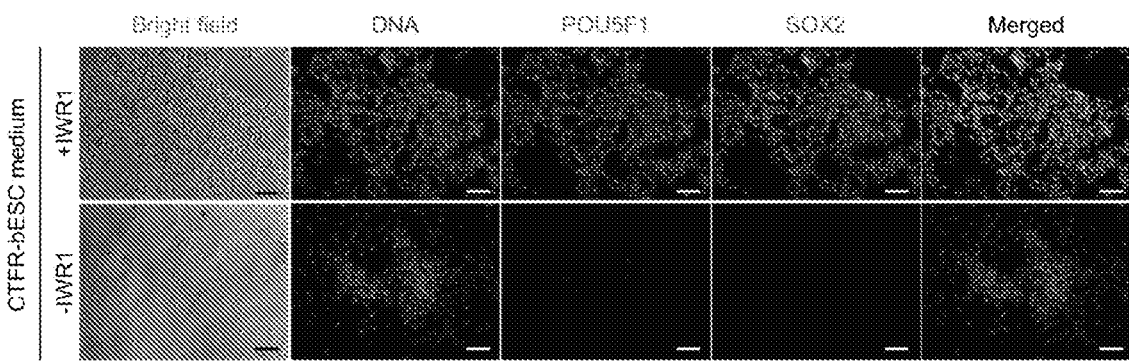
FIG. 3
| | | % Mapped reads | Uniquely mapped reads |
|---|---|---|---|
| CTFR-bESC Rep 1 | Input | 74.3 | 55,987,347 |
| | H3K4me3 | 60.7 | 15,340,811 |
| | H3K27me3 | 76.4 | 27,317,967 |
| CTFR-bESC Rep 2 | Input | 76.3 | 57,840,518 |
| | H3K4me3 | 60.1 | 16,400,918 |
| | H3K27me3 | 86.2 | 16,015,709 |
FIG. 4A
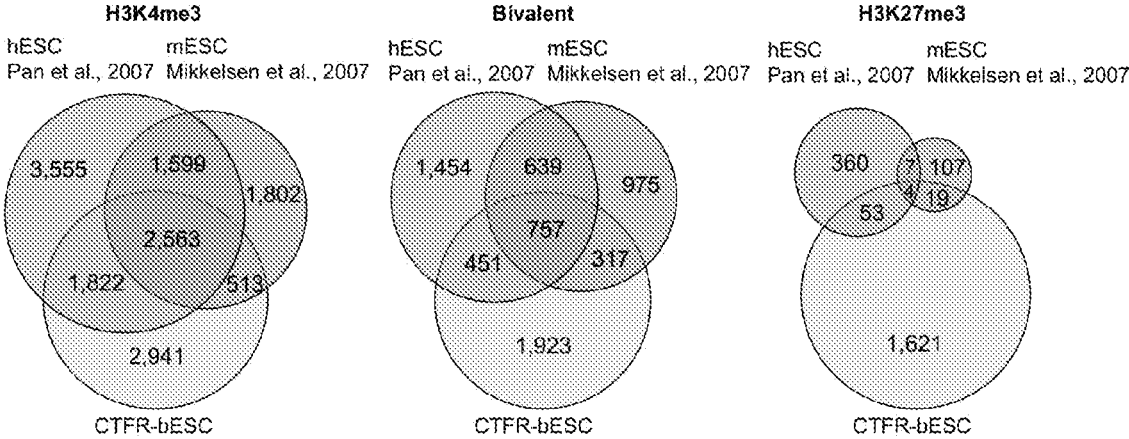
FIG. 4B

| CTFR-bESC-marked genes | Shared with hESC and mESC | Shared only with hESC | Shared only with mESCs | Total shared |
|---|---|---|---|---|
| Only H3K4me3 (n=7,839) | 2,563 (32.69%) | 1,822 (23.24%) | 513 (6.54%) | 4,898 (62.48%) |
| Bivalent domains (n=3,448) | 757 (21.95%) | 447 (12.96%) | 317 (9.19%) | 1,521 (44.11%) |
| Only H3K27me3 (n=1,697) | 4 (0.23%) | 53 (3.1%) | 19 (1.11%) | 76 (4.47%) |

| Naïve ESC markers | | Primed ESC markers | |
| --- | --- | --- | --- |
| Gene | CTFR-bESC | Gene | CTFR-bESC |
| FGF4 | 0 | SOX6 | 0.1 |
| DNMT3L | 0 | HOXB3 | 0.15 |
| DPPA3 | 0 | POU3F2 | 0.15 |
| HORMAD1 | 0 | RFX4 | 0.6 |
| TFCP2L1 | 0 | MYC | 0.65 |
| DPPA2 | 0 | DLL1 | 0.95 |
| ZFP42 | 0.1 | MEIS1 | 1.65 |
| TBX3 | 0.15 | LMO2 | 2.15 |
| MAEL | 0.55 | TET3 | 3.45 |
| DUSP10 | 1.4 | SOX1 | 6.1 |
| DUSP5 | 1.85 | ZIC1 | 7.05 |
| DUSP3 | 1.9 | CD47 | 7.65 |
| KLF4 | 2.2 | MEIS2 | 9.6 |
| CD44 | 2.85 | ZNF521 | 12.3 |
| NANOG | 3.35 | NCAM1 | 16.55 |
| TET2 | 4.55 | TET1 | 18.5 |
| TEAD4 | 5.05 | DUSP6 | 33.75 |
| KLF5 | 5.45 | ZIC3 | 33.15 |
| DUSP14 | 6.35 | DNMT3A | 48.1 |
| STAT3 | 7.05 | DNMT3B | 88.05 |
| TFE3 | 32.35 | ZIC2 | 127.35 |
| CD9 | 301.55 | OTX2 | 129.95 |

| | | No. processed embryos | No. established cell lines | Derivation efficiency |
|---|---|---|---|---|
| Plating Method | Whole blastocyst | 16 | 9 | 56% |
| | Mechanical isolation | 12 | 7 | 58% |
| | Immunosurgery | 16 | 7 | 44% |
| Embryo Source | IVM-IVF | 44 | 23 | 52% |
| | OPU-IVF Holstein | 6 | 6 | 100% |
| | OPU-IVF Jersey | 14 | 9 | 64% |
| | SCNT- Jersey | 4 | 3 | 75% |

FIG. 7A

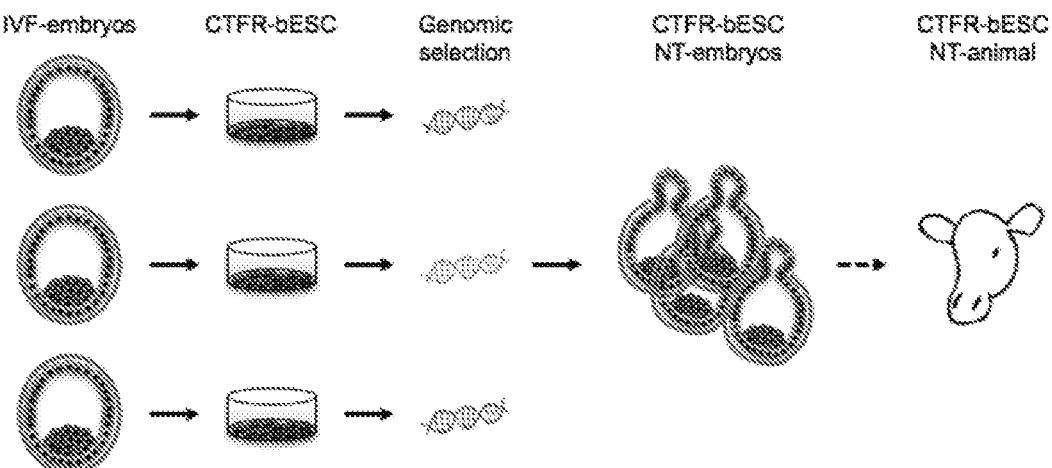

FIG. 7B

| | | No. of embryos in culture | No. of blastocysts | Derivation efficiency |
|---|---|---|---|---|
| bESC source | IVM-IVF | 46 | 9 | 20% |
| | Fibroblast control | 58 | 21 | 36% |
| | Holstein 1 OPU-IVF | 52 | 6 | 12% |
| | Holstein 2 OPU-IVF | 51 | 5 | 10% |
| | Fibroblast control | 46 | 15 | 33% |
| | Jersey OPU-IVF | 35 | 5 | 14% |
| | Jersey SCNT | 30 | 3 | 10% |
| | Fibroblast control | 44 | 7 | 16% |

FIG. 7C

Embryo production

In-vitro maturation IVF     In-vitro culture

GV oocyte   MII oocyte    Zygote     Day 7 blastocyst     ZP depleted blastocyst

Culture conditions

*Modified TeSR1 medium* (- TGFβ)

Inactivated MEF
+ FGF2 (20 ng/ml)
+ IWR1 (2.5 mM)

EFFICIENT DERIVATION OF STABLE PLURIPOTENT BOVINE EMBRYONIC STEM CELLS

CROSS-REFERENCE TO RELATED APPLICATION

This application is a national stage application under 35 U.S.C. § 371 of International Application No. PCT/US2019/013299, filed Jan. 11, 2019, which claims the benefit and priority under 35 U.S.C. § 119(e) of U.S. Provisional Application No. 62/616,975, filed Jan. 12, 2018, the contents of each of which are incorporated by reference herein in their entirety.

STATEMENT OF GOVERNMENT SUPPORT

This invention was made with Government support under Grant No. HD070044, awarded by the National Institutes of Health. The Government has certain rights in the invention.

BACKGROUND

Despite years of research, the derivation of stable pluripotent embryonic stem cells (ESCs) in the bovine species has been challenging. Most, if not all, of the reported bovine ESC lines do not pass the commonly used pluripotency tests, i.e. in-vitro differentiation assays, in-vivo teratoma formation and/or chimera formation. Moreover, they show poor derivation efficiencies, limited proliferation capacities, and loss of pluripotency markers after extensive passages. Thus a need exits in the art for methods to derive stable bovine pluripotent ESCs. This disclosure satisfies this need and provide related advantages as well.

SUMMARY OF THE DISCLOSURE

Provided herein are methods for producing stable ungulate embryonic stem cells (ESC), the methods comprising, or alternatively consisting essentially of, or yet further consisting of culturing an ungulate blastocyst cell or a pluripotent cell isolated from an embryo, in a cell culture media, the media comprising: (i) inactivated feeder cells; (ii) an effective amount of Fibroblast Growth Factor 2 (FGF2) or an equivalent thereof; and (iii) an effective amount of one or more of an inhibitor of Wnt signaling. In one aspect, the ungulate ESC, blastocyst cell or the or a pluripotent cell isolated from an embryo is bovine or an ovine cell. In a further aspect, the blastocyst cell, the pluripotent cell isolated from an embryo, or ESC is detectable labeled.

The steps of the method are not limited by any specific order. For example, one or more of the (i) inactivated feeder cells; (ii) the effective amount of Fibroblast Growth Factor 2 (FGF2) or an equivalent thereof; and (iii) the effective amount of the one or more inhibitors of Wnt signaling can be combined and then the blastocyst cell or the pluripotent cell is added to the culture. Alternatively, in one aspect, the one or more of (i), (ii), or (iii) is provided in the cell culture media after to the addition of the ungulate blastocyst or the pluripotent cell. Alternatively, the one or both of (ii) the effective amount of Fibroblast Growth Factor 2 (FGF2) or an equivalent thereof; and (iii) the effective amount of the one or more inhibitors of Wnt signaling are added to the blastocyst cell or the pluripotent cell on the inactivated feeder cells.

In a further aspect, the cell culture medium further comprises, or alternatively consists essentially of, or yet further consists of, an effective amount of a Rho-associated coiled-coil kinase (ROCK) inhibitor. Non-limiting examples of ROCK inhibitors include one or more of AS1892802, Fasudil hydrochloride, GSK 269962, GSK 429286, H1152, Glyclyl-H 1152, HA 1100, OXA 06, RKI 1447, SB 772077B, SR 3677, TC-S 7001, or Y-27632, or an equivalent of each thereof, or a combination thereof. In one aspect, the ROCK inhibitor is Y-27632 or an equivalent thereof. These are known in the art and are commercially available from Tocris Bioscience (tocris.com, last accessed on Jan. 11, 2018).

In a further aspect, cell culture medium further comprises an effective amount of a low fatty acid bovine serum albumin (BSA) or an equivalent thereof. Low fatty acid BSA is commercially available form Sigma-Aldrich (sigmaaldrich.com/catalog/product/sigma/a8806?lang=en&region=US, last accessed on Jan. 18, 2018). In a yet further aspect, the cell culture medium is modified TeSR™1 basal medium (e.g. lacking TGFβ). In yet a further aspect, the cell culture medium is TeSR™1 basal medium, N2B27, or E6 (available from Thermo-Fischer, catalog number A15164091).

In one aspect, the inactivated feeder cells are murine embryonic fibroblasts, or alternatively the inactivated feeder cells are replaced by an organic extracellular matrix or feeder cell conditioned medium. Non-limiting examples of an organic matrix is Matrigel® solubilized basement membrane matrix or vitronectin. In a yet further aspect, the inactivated feeder cells are replaced by an organic matrix and supplementation with an effective amount of Activin-A. Non-limiting examples of the organic matric is Vitronectin and Matrigel® solubilized basement membrane matrix.

In one aspect, the ungulate embryo from which the pluripotent cells are isolated has been prepared by a method comprising nuclear transfer cloning or parthenogenetic activation. In another aspect, the embryo has been prepared by a method comprising natural or artificial insemination. In a further aspect, the blastocyst cell is isolated from a preimplantation embryo, optionally a morula or a cleavage stage embryo. In another aspect, the pluripotent cell of the embryo is isolated from the embryonic disk of a post-hatch embryo.

In a yet further aspect, the ESCs are isolated from the cell culture media after being cultured for an effective amount of time. In addition, one can also isolate one or more microvesicles or exosomes from the culture media or the cells.

Further provided are methods for performing genomic selection, the method comprising, consisting essentially of, or yet further consisting of: (i) screening ungulate ESCs that have been produced according to the method as prepared above for a preferred genotype; and (ii) selecting ungulate ESCs comprising the preferred genotype. Preferred genotypes could relate to particular breeding or other agricultural traits, e.g., high milk production for bovines, for example or certain traits for meat production or quality, e.g., fat or protein content.

Further provided is a method of genetically modifying an ungulate, the method comprising, or alternatively consisting essentially of, or yet further consisting of, (a) establishing an embryo from a nuclear transfer process wherein the ungulate ESC as disclosed herein is inserted into an enucleated ungulate oocyte, and (b) implanting the embryo into a non-human recipient host. In a further aspect, the embryo is gestated in the recipient host. The resulting non-human animal and its offspring from the implanted embryo is further disclosed herein. In a yet further aspect, the method can further comprise introducing the ungulate ESC to a genetically modified embryo or an embryo produced by nuclear transfer cloning.

Yet further provided is a method of creating a chimeric non-human animal, the method comprising, or alternatively consisting essentially of, or yet further consisting of: (a) generation of ungulate ESC; (b) introduction of ungulate into a preimplantation embryo; and (c) transfer of embryo to a non-human recipient. Yet further provided is the non-human animal prepared by the method and the offspring from the ESC.

Yet further provided is a method for creating ungulate germ cells (sperm and oocytes) from ungulate ESC, the method comprising, or alternatively consisting essentially of, or yet further consisting of: (a) generating ungulate ESC; (b) in vitro differentiation of the ungulate ESC to germ cells by addition/subtraction of growth factors and/or co-culture with somatic cells; (or) (c) transplantation of the ungulate ESC or intermediate differentiated cells into an non-human animal for generation of germ cells. In one aspect, the ungulate ESC are transplanted to a germline-deficient non-human embryo. In a further aspect, the ungulate ESC are transplanted to a non-bovine animal or a bovine animal. Yet further provided are the non-human animals prepared by these methods, as well the offspring from the transplanted ESC.

Further provided are compositions, cells, microvesicles, exosomes and non-human animals as well as their offspring prepared by the above methods. In one aspect, provided herein is the ungulate ESC produced according to the methods as well as populations of the ungulate ESCs produced by the methods.

This disclosure also provides a microvesicle or exosome isolated from the cells or culture media produced by these methods as well as populations of the microvesicle or exosomes produced by the cells produced by methods of this disclosure.

In a further aspect, the compositions further comprise a carrier such as a pharmaceutically acceptable carrier. In a further aspect, the compositions also comprise a cryopreservative or a preservative.

BRIEF DESCRIPTION OF THE FIGURES

FIGS. 1A-1D: Derivation and characterization of CTFR-bESCs. (FIG. 1A) Bright field images and alkaline phosphatase staining showing typical colony morphologies of CTFR-bESCs (note that feeder layer is negative for alkaline phosphatase). (FIG. 1B) Immunofluorescence staining for SOX2, OCT4, GATA6, and CDX2 markers in bovine blastocysts (top) and CTFR-bESCs (bottom). P24, passage 24. (FIG. 1C) Expression analysis of inner cell mass (ICM), trophectoderm (TE), and primitive endoderm (PE) lineage-specific markers in CTFR-bESCs, whole blastocysts, and fibroblasts. Transcriptome analysis was done using RNA-seq. Samples include two independent lines of CTFR-bESCs (>P30), two independent pools of whole blastocysts (10 each), and two lines of bovine fibroblasts. Color scale goes from red (high expression) to green (low to no expression). (FIG. 1D) Representative images showing hematoxylin and eosin staining of histological sections derived from teratomas generated by CTFR-bESCs. CTFR-bESC-derived teratomas contained tissues from all three germ lineages: ectoderm, endoderm and mesoderm.

FIGS. 2A-2H: Derived CTFR-bESCs are stable and pluripotent. (FIG. 2A) Normal karyotype (2N=60 chromosomes) observed in CTFR-bESCs at P34. (FIG. 2B) Average population-doubling time for two CTFR-bESC lines at passages P13, P23, P35, and P45. Bar denotes mean±SEM. (FIG. 2C) Principal component analysis of RNA-seq data from two lines of CTFR-bESCs collected at different passages (CTFR-bESC A at P13, P23, P35, P45 and CTFR-bESC B at P13, P24, P35 and P46), two whole bovine blastocysts, and two bovine fibroblast cell lines. Blue circle indicates all CTFR-bESC lines are clustered together irrespective of the passage number. Red circle indicates blastocysts and green circle indicates fibloblast cell lines. (FIG. 2D) Heatmap showing global transcriptomic analysis of CTFR-bESC A at P13, P23, P35, P45; and CTFR-bESC B at P13, P24, P35 and P46, two whole bovine blastocysts (BL A and BL B) and two bovine fibroblast cell lines (Fib A and Fib B). (FIG. 2E) Expression analysis of specific inner cell mass (ICM), trophectoderm (TE), and primitive endoderm (PE) lineage-specific markers in CTFR-bESC A at P13, P23, P35, P45 and CTFR-bESC B at P13, P24, P35 and P46, whole blastocysts, and fibroblasts. Transcriptome analysis was performed using RNA-seq and RPKM values are shown. Color scale goes from red (high expression) to green (low to no expression). (FIG. 2F) Immunofluorescence staining for SOX2 (green) and POU5F1 (red) in CTFR-bESCs at P11, P21, P33 and P43. (FIG. 2G) Teratomas obtained from two different lines of CTFR-bESCs (A and B) 8 weeks after injection of 1×10⁶ cells in the leg muscle of NSG SCID mice. (FIG. 2H) Immunofluoresence staining for TUJ1, FOXA2, and ASM indicated that bESC-derived teratomas express markers of the three germ layers.

FIG. 3: Inhibition of the canonical Wnt-signaling pathway is a requirement for self-renewal of pluripotent CTFR-bESCs. Immunostaining of the core pluripotency markers POU5F1 and SOX2 in bovine embryonic stem cells grown in medium supplemented with or devoid of IWR1 (+IWR1 and −IWR1, respectively). Cells were grown for four passages in the two conditions before immunofluorescence analysis. Scale bar 100 μm.

FIGS. 4A-4C. ChIP-seq analysis and comparison of CTFR-bESC histone methylation landscape with human and mouse ESCs. (FIG. 4A) Reads were mapped to the UMD3.1 bovine reference genome using bwa-aln. Percentages of mapped reads and total number of uniquely mapped reads used for peak calling are shown for input, H3K4me3, and H3K27me3 samples for two biological replicates. (FIG. 4B) Venn diagrams showing the overlap between H3K4me3-, H3K27me3-, and bivalent-genes found in mice, human, and CTFR-bESCs (FIG. 4C), which includes the total number of genes and percentages of overlap across species per epigenetic category.

FIGS. 5A-5C: Histone methylation landscape of CTFR-bESCs. (FIG. 5A) Transcriptional status of genes containing H3K4me3. H3K27me3 or bivalent domains. Genes with RPKM≥0.4 were considered expressed while genes with RPKM<0.4 were non-expressed. Mean RPKM±SEM values of expressed genes are shown inside the bar plot, and mean RPKM±SEM for all genes (expressed and non-expressed) are shown in the x-axis. (FIG. 5B) Functional characterization of genes containing H3K4me3 (n=8,816), H3K27me3 (n=2,553), or bivalent domains (n=3,886). The top-ten GO terms are shown. Bar plot shows the −log₁₀ of the P-value for selected biological processes GO terms from DAVID. (FIG. 5C) Genome browser snapshot of genes containing H3K4me3 (TGFBR1, FGF8, SALL4, TRIM8, SBDS, and TAF8), H3K27me3 (OOEP, REC8, SLITRK4, LRRC4B, ARRX, and CSNB1), or bivalent domains (WNT2, WNT7A, MATN2, CHL1, MSX2, and ETV4). H3K4me3-, H3K27me3-, and bivalent-selected genes were associated with three different GO terms. Start of the gene is denoted with a black arrow.

(FIG. 6A) Transcriptome analysis of selected naïve and primed pluripotency markers in CTFR-bESCs. RNA-seq was performed and reads per kilobase per million (RPKM) values were used to define expressed (RPKM≥0.4, red color) and non-expressed genes (RPKM<0.4, green color). Mean of two biological replicates are shown. (FIG. 6B) Genome browser snapshots of H3K4me3- and H3K27me3-marks in core pluripotency genes (OCT4, SOX2, NANOG, SALL4) in CTFR-bESCs. (FIG. 6C) Genome browser snapshots of histone methylation profiles of primed and naïve pluripotency markers in CTFR-bESCs. (FIG. 6D) Analysis of CTFR-GFP-bESC integration after microinjecteion of cells into bovine morula embryos. Injected embryos were cultured in vitro for 3 days and blastocysts were assessed for CTFR-GFP-bESC presence.

FIGS. 7A-7C: Potential applications of CTFR-bESCs for genomic selection. (FIG. 7A) CTFR-bESC derivation efficiency using three different plating methods (whole blastocyst, mechanical isolation of ICM, and immunosurgery-derived ICM) and embryo sources (IVM-IVF, OPU-IVF, SCNT, Holstein and Jersey breeds). Derivation efficiency was measured as the percentage of blastocysts that give rise to a stable CTFR-bESC line at P3 over the total number of embryos seeded per method. IVM, in vitro matured slaughterhouse-derived oocytes; OPU, ovum pick-up-derived oocytes; IVF, in vitro fertilization; SCNT, somatic cell nuclear transfer. Jersey and Holstein, breeds. (FIG. 7B) A schematic diagram showing the strategy of using CTFR-bESCs for genomic selection to produce animals of superior genetic value through high efficient CTFR-bESC derivation and NT. (FIG. 7C) CTFR-bESC generated from different sources can be used as nuclear donors for cloning. IVM, in vitro matured slaughterhouse-derived oocytes; OPU, ovum pick-up-derived oocytes; IVF, in vitro fertilization; SCNT, somatic cell nuclear transfer. Jersey and Holstein, breeds.

(FIG. 8A) Representative images of explants at the time of plating (day 0), outgrowths (day 7), and first passage (CTFR-bESC P1) (day 14) for three different plating methods. (FIG. 8B) Flow cytometric analysis of cell cycle in bovine fibroblasts, serum-starved-bovine fibroblasts, and CTFR-bESCs. (FIG. 8C) Immunofluorescence analysis of SOX2 and POU5F1 markers in CTFR-bESCs derived from CTFR-bESC-NT embryos.

(FIG. 10A) Morphology, alkaline phosphatase stainig and karyotype of ovine ESCs (oESCs) cultured in CTFR medium (CTFR-oESCs) for 25 to 41 passages. (FIG. 10B) Flow cytometric analysis of cell cycle in two lines of CTFR-oESCs and ovine fibroblasts. (FIG. 10C). Immuno-fluorescence staining for SOX2, OCT4, GATA6, and CDX2 markers in ovine blastocysts (top) and CTFR-oESCs (bottom) at passage 22 (P22) and P44 (FIG. 10D). Quantitative real-time RT-PCR analysis of gene expression for different genes in tissues, embryos and CTFR-oESCs from sheep.

DETAILED DESCRIPTION

Definitions

Figure 1A:
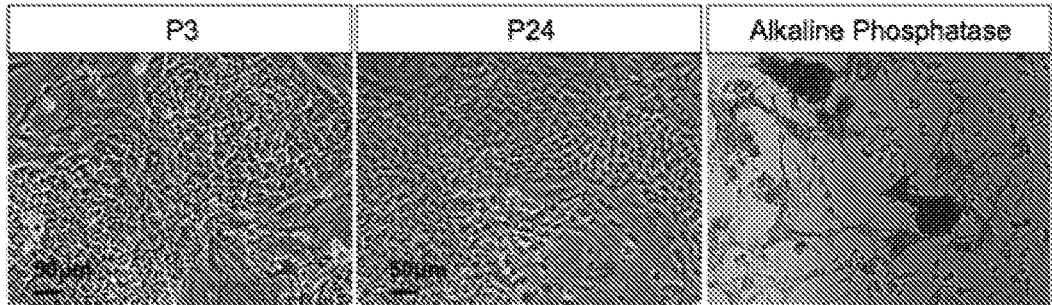

The practice of the present invention will employ, unless otherwise indicated, conventional techniques of tissue culture, immunology, molecular biology, microbiology, cell biology and recombinant DNA, which are within the skill of the art. See, e.g., Sambrook, Fritsch and Maniatis (1989) Molecular Cloning: A Laboratory Manual, $2^{nd}$ edition; F. M. Ausubel, et al. eds. (1987) Current Protocols In Molecular Biology; the series Methods in Enzymology (Academic Press, Inc.): PCR 2: A Practical Approach (1995) (M. J. MacPherson, B. D. Hames and G. R. Taylor eds.); Harlow and Lane, eds. (1988) Antibodies, A Laboratory Manual; Harlow and Lane, eds. (1999) Using Antibodies, A Laboratory Manual; and R. I. Freshney, ed. (1987) Animal Cell Culture.

All numerical designations, e.g., pH, temperature, time, concentration, and molecular weight, including ranges, are approximations which are varied (+) or (−) by increments of 1.0 or 0.1, as appropriate. It is to be understood, although not always explicitly stated that all numerical designations are preceded by the term "about". It also is to be understood, although not always explicitly stated, that the reagents described herein are merely exemplary and that equivalents of such are known in the art.

As used in the specification and claims, the singular form "a," "an" and "the" include plural references unless the context clearly dictates otherwise.

The terms autologous transfer, autologous transplantation, autograft and the like refer to treatments wherein the cell donor is also the recipient of the cell replacement therapy. The terms allogeneic transfer, allogeneic transplantation, allograft and the like refer to treatments wherein the cell donor is of the same species as the recipient of the cell replacement therapy, but is not the same individual. A cell transfer in which the donor's cells and have been histocompatibly matched with a recipient is sometimes referred to as a syngeneic transfer. The terms xenogeneic transfer, xenogeneic transplantation, xenograft and the like refer to treatments wherein the cell donor is of a different species than the recipient of the cell replacement therapy.

"Clonal proliferation" refers to the growth of a population of cells by the continuous division of single cells into two identical daughter cells and/or population of identical cells.

As used herein, the term "microRNAs" or "miRNAs" refers to post-transcriptional regulators that typically bind to complementary sequences in the three prime untranslated regions (3' UTRs) of target messenger RNA transcripts (mRNAs), usually resulting in gene silencing. Typically, miRNAs are short, non-coding ribonucleic acid (RNA) molecules, for example, 21 or 22 nucleotides long. The terms "microRNA" and "miRNA" are used interchangeably.

As used herein "lyophilization" intends low temperature drying or freeze drying.

Cell-derived exosomes or microvesicles, also referred to as extracellular exosomes or microvesicles, are membrane surrounded structures that are released by cells in vitro and in vivo. Extracellular exosomes or microvesicles can contain proteins, lipids, and nucleic acids and can mediate intercellular communication between different cells, including different cell types, in the body. Two types of extracellular exosomes or microvesicles are exosomes or microvesicles and microvesicles. Exosomes or microvesicles are small lipid-bound, cellularly secreted exosomes or microvesicles that mediate intercellular communication via cell-to-cell transport of proteins and RNA (El Andaloussi, S. et al. (2013) Nature Reviews: Drug Discovery 12(5):347-357). Exosomes or microvesicles range in size from approximately 30 nm to about 200 nm. Exosomes or microvesicles are released from a cell by fusion of multivesicular endosomes (MVE) with the plasma membrane. Microvescicles, on the other hand, are released from a cell upon direct budding from the plasma membrane (PM) and are packaged with different factors. Microvesicles are typically larger than exosomes or microvesicles and range from approximately 200 nm to 1 μm and have different functionalities.

Cell-derived exosomes or microvesicles can be isolated from eukaryotic cells using commercially available kits as disclosed herein and available from biovision.com and novusbio.com, or using the methods described herein. Non-limiting examples of cells that cell-derived exosomes or microvesicles can be isolated from include stem cells. Non-limiting examples of such stem cells include adult stem cells, embryonic stem cells, embryonic-like stem cells, non-embryonic stem cells, or induced pluripotent stem cells.

As used herein, the terms "overexpress," "overexpression," and the like are intended to encompass increasing the expression of a nucleic acid or a protein to a level greater than the exosome or microvesicle naturally contains. It is intended that the term encompass overexpression of endogenous, as well as heterologous nucleic acids and proteins.

As used herein, the term "homogeneous" in reference to a population of e cell-derived exosomes or microvesicles refers to population of cell-derived exosomes or microvesicles that have a similar amount of an exogenous nucleic acid, a similar amount of an exogenous protein, are of a similar size, or combinations thereof. A homogenous population is one wherein about 65%, about 70%, about 75%, about 80%, about 85%, about 90%, about 95%, about 98%, or 100% of the cells or the cell-derived exosomes or microvesicles share at least one characteristic.

As used herein, the term "heterogeneous" in reference to a population of cells or cell-derived exosomes or microvesicles refers to population of cells or cell-derived exosomes or microvesicles that have differing amounts of an indentifying phenotype or marker, or differing amounts of an exogenous protein, are of a different size, or combinations thereof.

The term "substantially" refers to the complete or nearly complete extent or degree of a characteristic and in some aspects, defines the purity of the isolated or purified population of cells, exosomes or microvesicles.

The term "purified population," relative to cell populations, cell-derived exosomes or microvesicles or miRNA, as used herein refers to plurality of such that have undergone one or more processes of selection for the enrichment or isolation of the desired cell type, exosome or microvesicle or miRNA population relative to some or all of some other component with which the cell, cell-derived exosomes or microvesicles are normally found in culture media. Alternatively, "purified" can refer to the removal or reduction of residual undesired components found in the conditioned media (e.g., cell debris, soluble proteins, etc.). A "highly purified population" as used herein, refers to a population of cells or cell-derived exosomes or microvesicles in which at least 65%, at least 70%, at least 75%, at least 80%, at least 85%, at least 90%, at least 95%, at least 98%, at least 99% or 100% of cell debris and soluble proteins in the conditioned media along with the cells, cell-derived exosomes or microvesicles or miRNA are removed. The cells, populations, exosomes or microvesicles and miRNA as described herein can be provided in isolated, purified, highly purified forms, homogeneous, substantially homogeneous and heterogenous forms.

As used herein the terms "culture media" and "culture medium" are used interchangeably and refer to a solid or a liquid substance used to support the growth of cells (e.g., stem cells). Preferably, the culture media as used herein refers to a liquid substance capable of maintaining stem cells in an undifferentiated state. The culture media can be a water-based media which includes a combination of ingredients such as salts, nutrients, minerals, vitamins, amino acids, nucleic acids, proteins such as cytokines, growth factors and hormones, all of which are needed for cell proliferation and are capable of maintaining stem cells in an undifferentiated state. For example, a culture media can be a synthetic culture media such as, for example, minimum essential media a (MEM-α) (HyClone Thermo Scientific, Waltham, MA, USA), DMEM/F12, GlutaMAX (Life Technologies, Carlsbad, CA, USA), Neurobasal Medium (Life Technologies, Carlsbad, CA, USA), KO-DMEM (Life Technologies, Carlsbad, CA, USA), DMEM/F12 (Life Technologies, Carlsbad, CA, USA), supplemented with the necessary additives as is further described herein. In some embodiments, the cell culture media can be a mixture of culture media. Preferably, all ingredients included in the culture media of the present disclosure are substantially pure and tissue culture grade. "Conditioned medium" and "conditioned culture medium" are used interchangeably and refer to culture medium that cells have been cultured in for a period of time and wherein the cells release/secrete components (e.g., proteins, cytokines, chemicals, etc.) into the medium.

A "composition" is also intended to encompass a combination of a cell, a cell population, an exosome or microvesicle, an miRNA, or populations of such, or an active agent, and another carrier, e.g., compound or composition, inert (for example, a detectable agent or label) or active, such as an adjuvant, diluent, binder, stabilizer, buffers, salts, lipophilic solvents, preservative, adjuvant or the like. Carriers also include biocompatible scaffolds, pharmaceutical excipients and additives proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. Carbohydrate excipients are also intended within the scope of this invention, examples of which include but are not limited to monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and myoinositol.

A preservative intends a composition that enhances the viability of an agent in a composition. Non-limiting examples include benzoates (such as sodium benzoate, benzoic acid), nitrites (such as sodium nitrite) and sulphites (such as sulphur dioxide).

A cryoprotective is a compound that protects the agent during freezing and thawing procedures. Non-limiting examples of such include DMSO, glycerol, and polyethylene glycol (PEG).

A "control" is an alternative subject or sample used in an experiment for comparison purpose. A control can be "positive" or "negative". For example, where the purpose of the experiment is to determine a correlation of an altered expression level of a gene with a particular phenotype, it is generally preferable to use a positive control (a sample from a subject, carrying such alteration and exhibiting the desired phenotype), and a negative control (a subject or a sample from a subject lacking the altered expression or phenotype). Additionally, when the purpose of the experiment is to determine if an agent effects the differentiation of a stem cell or expression of an exosome or microvesicle or miRNA, it is preferable to use a positive control (a sample with an aspect that is known to affect differentiation or altered expression) and a negative control (an agent known to not have an affect or a sample with no agent added).

The term "culturing" refers to the in vitro propagation of cells or organisms on or in media of various kinds. It is understood that the descendants of a cell grown in culture may not be completely identical (i.e., morphologically, genetically, or phenotypically) to the parent cell. By "expanded" is meant any proliferation or division of cells.

As used herein, the term "detectably labeled" means that the agent (biologic or small molecule) is attached to another molecule, compound or polymer that facilitates detection of the presence of the agent in vitro or in vivo.

A "detectable label" intends a directly or indirectly detectable compound or composition that is conjugated directly or indirectly to the composition to be detected, e.g., N-terminal histidine tags (N-His), magnetically active isotopes, e.g., $^{115}$Sn, $^{117}$Sn and $^{119}$Sn, a non-radioactive isotopes such as $^{13}$C and $^{15}$N, polynucleotide or protein such as an antibody so as to generate a "labeled" composition. The term also includes sequences conjugated to the polynucleotide that will provide a signal upon expression of the inserted sequences, such as green fluorescent protein (GFP) and the like. The label may be detectable by itself (e.g. radioisotope labels or fluorescent labels) or, in the case of an enzymatic label, may catalyze chemical alteration of a substrate compound or composition which is detectable. The labels can be suitable for small-scale detection or more suitable for high-throughput screening. As such, suitable labels include, but are not limited to magnetically active isotopes, non-radioactive isotopes, radioisotopes, fluorochromes, luminescent compounds, dyes, and proteins, including enzymes. The label may be simply detected or it may be quantified. A response that is simply detected generally comprises a response whose existence merely is confirmed, whereas a response that is quantified generally comprises a response having a quantifiable (e.g., numerically reportable) value such as an intensity, polarization, and/or other property. In luminescence or fluorescence assays, the detectable response may be generated directly using a luminophore or fluorophore associated with an assay component actually involved in binding, or indirectly using a luminophore or fluorophore associated with another (e.g., reporter or indicator) component.

Examples of luminescent labels that produce signals include, but are not limited to bioluminescence and chemiluminescence. Detectable luminescence response generally comprises a change in, or an occurrence of, a luminescence signal. Suitable methods and luminophores for luminescently labeling assay components are known in the art and described for example in Haugland, Richard P. (1996) Handbook of Fluorescent Probes and Research Chemicals ($6^{th}$ ed.). Examples of luminescent probes include, but are not limited to aequorin and luciferases.

Examples of suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, and Texas Red. Other suitable optical dyes are described in the Haugland, Richard P. (1996) Handbook of Fluorescent Probes and Research Chemicals ($6^{th}$ ed.).

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in a eukaryotic cell.

"Differentially expressed" intends an up- or downward expression of a gene, exosome or microvesicle, or marker, for example, as compared to a control. In one aspect, a control is a differentiated cell as compared to a pluripotent or stem cell. "Differentially expressed" as applied to a gene, protein, cell, population, exosome or microvesicle, miRNA, or marker, refers to the differential production of the product as compared to a control such as expression level found in the native environment. Differently expressed is mRNA transcribed from the gene or the protein product encoded by the gene. A differentially expressed gene may be overexpressed or underexpressed (a.k.a. inhibited) as compared to the expression level of a normal, non-treated, native or control cell. In one aspect, it refers to overexpression that is 1.5 times, or alternatively, 2 times, or alternatively, at least 2.5 times, or alternatively, at least 3.0 times, or alternatively, at least 3.5 times, or alternatively, at least 4.0 times, or alternatively, at least 5 times, or alternatively 10 times higher (i.e., and therefore overexpressed) or lower than the expression level detected in a control sample. The term "differentially expressed" also refers to nucleotide sequences in a cell or tissue which are expressed where silent in a control cell or not expressed where expressed in a control cell.

The term "stem cell" refers to a cell that is in an undifferentiated or partially differentiated state and has the capacity for self-renewal and/or to generate differentiated progeny. Self-renewal is defined as the capability of a stem cell to proliferate and give rise to more such stem cells, while maintaining its developmental potential (i.e., totipotent, pluripotent, multipotent, etc.). The term "somatic stem cell" is used herein to refer to any stem cell derived from non-embryonic tissue, including fetal, juvenile, and adult tissue. Natural somatic stem cells have been isolated from a wide variety of adult tissues including blood, bone marrow, brain, olfactory epithelium, skin, pancreas, skeletal muscle, and cardiac muscle. Exemplary naturally occurring somatic stem cells include, but are not limited to, mesenchymal stem cells (MSCs) and neural stem cells (NSCs). In some embodiments, the stem or progenitor cells can be embryonic stem cells. As used herein, "embryonic stem cells" refers to stem cells derived from tissue formed after fertilization but before the end of gestation, including pre-embryonic tissue (such as, for example, a blastocyst), embryonic tissue, or fetal tissue taken any time during gestation, typically but not necessarily before approximately 10-12 weeks gestation. Most frequently, embryonic stem cells are pluripotent cells derived from the early embryo or blastocyst. Embryonic stem cells can be obtained directly from suitable tissue, including, but not limited to human tissue, or from established embryonic cell lines. "Embryonic-like stem cells" refer to cells that share one or more, but not all characteristics, of an embryonic stem cell.

"Differentiation" describes the process whereby an unspecialized cell acquires the features of a specialized cell such as a heart, liver, or muscle cell. "Directed differentiation" refers to the manipulation of stem cell culture conditions to induce differentiation into a particular cell type. "Dedifferentiated" defines a cell that reverts to a less committed position within the lineage of a cell. As used herein, the term "differentiates or differentiated" defines a cell that takes on a more committed ("differentiated") position within the lineage of a cell. As used herein "a cell that differentiates into a mesodermal (or ectodermal or endodermal) lineage" defines a cell that becomes committed to a specific mesodermal, ectodermal or endodermal lineage, respectively. Examples of cells that differentiate into a mesodermal lineage or give rise to specific mesodermal cells include, but are not limited to, cells that are adipogenic, leiomyogenic, chondrogenic, cardiogenic, dermatogenic, hematopoetic, hemangiogenic, myogenic, nephrogenic, urogenitogenic, osteogenic, pericardiogenic, or stromal.

As used herein, the term "differentiates or differentiated" defines a cell that takes on a more committed ("differentiated") position within the lineage of a cell. "Dedifferentiated" defines a cell that reverts to a less committed position within the lineage of a cell. Induced pluripotent stem cells are examples of dedifferentiated cells.

As used herein, the "lineage" of a cell defines the heredity of the cell, i.e. its predecessors and progeny. The lineage of a cell places the cell within a hereditary scheme of development and differentiation.

A "multi-lineage stem cell" or "multipotent stem cell" refers to a stem cell that reproduces itself and at least two further differentiated progeny cells from distinct developmental lineages. The lineages can be from the same germ layer (i.e. mesoderm, ectoderm or endoderm), or from different germ layers. An example of two progeny cells with distinct developmental lineages from differentiation of a multilineage stem cell is a myogenic cell and an adipogenic cell (both are of mesodermal origin, yet give rise to different tissues). Another example is a neurogenic cell (of ectodermal origin) and adipogenic cell (of mesodermal origin).

A "precursor" or "progenitor cell" intends to mean cells that have a capacity to differentiate into a specific type of cell. A progenitor cell may be a stem cell. A progenitor cell may also be more specific than a stem cell. A progenitor cell may be unipotent or multipotent. Compared to adult stem cells, a progenitor cell may be in a later stage of cell differentiation. An example of progenitor cell includes, without limitation, a progenitor nerve cell.

As used herein, a "pluripotent cell" defines a less differentiated cell that can give rise to at least two distinct (genotypically and/or phenotypically) further differentiated progeny cells. In another aspect, a "pluripotent cell" includes an Induced Pluripotent Stem Cell (iPSC) which is an artificially derived stem cell from a non-pluripotent cell, typically an adult somatic cell, that has historically been produced by inducing expression of one or more stem cell specific genes. Such stem cell specific genes include, but are not limited to, the family of octamer transcription factors, i.e. Oct-3/4; the family of Sox genes, i.e., Sox1, Sox2, Sox3, Sox 15 and Sox 18; the family of Klf genes, i.e. Klf1, Klf2, Klf4 and Klf5; the family of Myc genes, i.e. c-myc and L-myc; the family of Nanog genes, i.e., OCT4, NANOG and REX1; or LIN28. Examples of iPSCs are described in Takahashi et al. (2007) Cell advance online publication 20 Nov. 2007; Takahashi & Yamanaka (2006) Cell 126:663-76; Okita et al. (2007) Nature 448:260-262; Yu et al. (2007) Science advance online publication 20 Nov. 2007; and Nakagawa et al. (2007) Nat. Biotechnol. Advance online publication 30 Nov. 2007.

"Embryoid bodies or EBs" are three-dimensional (3D) aggregates of embryonic stem cells formed during culture that facilitate subsequent differentiation. When grown in suspension culture, EBs cells form small aggregates of cells surrounded by an outer layer of visceral endoderm. Upon growth and differentiation, EBs develop into cystic embryoid bodies with fluid-filled cavities and an inner layer of ectoderm-like cells.

An "induced pluripotent cell" intends embryonic-like cells reprogrammed to the immature phenotype from adult cells. Various methods are known in the art, e.g., "A simple new way to induce pluripotency: Acid." Nature, 29 Jan. 2014 and available at sciencedaily.com/releases/2014/01/140129184445, last accessed on Feb. 5, 2014 and U.S. Patent Application Publication No. 2010/0041054. Human iPSCs also express stem cell markers and are capable of generating cells characteristic of all three germ layers.

A "parthenogenetic stem cell" refers to a stem cell arising from parthenogenetic activation of an egg. Methods of creating a parthenogenetic stem cell are known in the art. See, for example, Cibelli et al. (2002) Science 295(5556): 819 and Vrana et al. (2003) Proc. Natl. Acad. Sci. USA 100(Suppl. 1)11911-6.

As used herein, the term "pluripotent gene or marker" intends an expressed gene or protein that has been correlated with an immature or undifferentiated phenotype, e.g., Oct 3/4, Sox2, Nanog, c-Myc and LIN-28. Methods to identify such are known in the art and systems to identify such are commercially available from, for example, EMD Millipore (MILLIPLEX® Map Kit).

Rho-associated kinase (ROCK) inhibitors intend Rho-associated protein kinase (ROCK) is a kinase belonging to the AGC (PKA/PKG/PKC) family of serine-threonine kinases. It is involved mainly in regulating the shape and movement of cells by acting on the cytoskeleton. Non-limiting examples of such include Thiazovivin or Y27632, which both can be purchased from Stemcell Technologies and respectively; SR3677, which can be purchased from tocris.com; and GSK429286, which can be purchased from Tocris Bioscience (tocris.com, last accessed on Jan. 11, 2018).

The term "isolated" as used herein refers to molecules or biological or cellular materials being substantially free from other materials, e.g., greater than 70%, or 80%, or 85%, or 90%, or 95%, or 98%. In one aspect, the term "isolated" refers to nucleic acid, such as DNA, RNA, miRNA, exosome or microvesicle, protein or polypeptide, or cell or cellular organelle, or tissue or organ, separated from other DNA, RNA, miRNA, exosome or microvesicle, protein or polypeptide, or cell or cellular organelle, or tissue or organ, respectively, that are present in the natural source and which allow the manipulation of the material to achieve results not achievable where present in its native or natural state, e.g., recombinant replication or manipulation by mutation. The term "isolated" also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments that are not naturally occurring as fragments and would not be found in the natural state. The term "isolated" is also used herein to refer to polypeptides which are isolated from other cellular proteins and is meant to encompass both purified and recombinant polypeptides, e.g., with a purity greater than 70%, or 80%, or 85%, or 90%, or 95%, or 98%. The term "isolated" is also used herein to refer to cells, exosomes or microvesicles, miRNA, or tissues that are isolated from other cells, exosomes or microvesicles, miRNA, or tissues and is meant to encompass both cultured and engineered cells or tissues and products produced or isolated from such.

The term "phenotype" refers to a description of an individual's trait or characteristic that is measurable and that is expressed only in a subset of individuals within a population. In one aspect of the invention, an individual's phenotype includes the phenotype of a single cell, a substantially homogeneous population of cells, a population of differentiated cells, or a tissue comprised of a population of cells.

The term pharmaceutically acceptable carrier (or medium), which may be used interchangeably with the term biologically compatible carrier or medium, refers to reagents, cells, compounds, materials, compositions, and/or dosage forms that are not only compatible with the cells and other agents to be administered therapeutically, but also are, within the scope of sound medical judgment, suitable for use in contact with the tissues of human beings and animals without excessive toxicity, irritation, allergic response, or other complication commensurate with a reasonable benefit/ risk ratio. Pharmaceutically acceptable carriers suitable for use in the present invention include liquids, semi-solid (e.g., gels) and solid materials (e.g., cell scaffolds and matrices, tubes sheets and other such materials as known in the art and described in greater detail herein). These semi-solid and solid materials may be designed to resist degradation within the body (non-biodegradable) or they may be designed to degrade within the body (biodegradable, bioerodable). A biodegradable material may further be bioresorbable or bioabsorbable, i.e., it may be dissolved and absorbed into bodily fluids (water-soluble implants are one example), or degraded and ultimately eliminated from the body, either by conversion into other materials or breakdown and elimination through natural pathways.

A population of cells intends a collection of more than one cell, exosome or microvesicle, or miRNA that is identical (clonal) or non-identical in phenotype and/or genotype. The population can be purified, highly purified, substantially homogenous or heterogeneous as described herein.

The term "propagate" means to grow or alter the phenotype of a cell or population of cells. The term "growing" refers to the proliferation of cells in the presence of supporting media, nutrients, growth factors, support cells, or any chemical or biological compound necessary for obtaining the desired number of cells or cell type. In one embodiment, the growing of cells results in the regeneration of tissue.

The term "effective amount" refers to a concentration or amount of a reagent or composition, such as a composition as described herein, cell population or other agent, that is effective for producing an intended result, including cell growth and/or differentiation in vitro or in vivo, or for the treatment of a condition as described herein. It will be appreciated that the number of cells to be administered will vary depending on the specifics of the disorder to be treated, including but not limited to size or total volume/surface area to be treated, as well as proximity of the site of administration to the location of the region to be treated, among other factors familiar to the medicinal biologist.

The terms effective period (or time) and effective conditions refer to a period of time or other controllable conditions (e.g., temperature, humidity for in vitro methods), necessary or preferred for an agent or composition to achieve its intended result, e.g., the differentiation or dedifferentiation of cells to a pre-determined cell type.

A "subject," "individual" or "patient" is used interchangeably herein, and refers to a vertebrate, preferably a mammal, more preferably a human. Mammals include, but are not limited to, murines, rats, simians, bovines, canines, felines, humans, farm animals, sport animals and pets.

"Substantially homogeneous" describes a population of cells in which more than about 50%, or alternatively more than about 60%, or alternatively more than 70%, or alternatively more than 75%, or alternatively more than 80%, or alternatively more than 85%, or alternatively more than 90%, or alternatively, more than 95%, of the cells are of the same or similar phenotype. Phenotype can be determined by a pre-selected cell surface marker or other marker.

As used herein, the terms "treating," "treatment" and the like are used herein to mean obtaining a desired pharmacologic and/or physiologic effect. The effect can be prophylactic in terms of completely or partially preventing a disorder or sign or symptom thereof, and/or can be therapeutic in terms of a partial or complete cure for a disorder and/or adverse effect attributable to the disorder. Examples of "treatment" include but are not limited to: preventing a disorder from occurring in a subject that may be predisposed to a disorder, but has not yet been diagnosed as having it; inhibiting a disorder, i.e., arresting its development; and/or relieving or ameliorating the symptoms of disorder.

"Administration" or "delivery" of a cell, exosome or microvesicle, miRNA, therapeutic or other agent and compositions containing same can be effected in one dose, continuously or intermittently throughout the course of treatment. Methods of determining the most effective means and dosage of administration are known to those of skill in the art and will vary with the composition used for therapy, the purpose of the therapy, the target cell being treated, and the subject being treated. Single or multiple administrations can be carried out with the dose level and pattern being selected by the treating physician or in the case of animals, by the treating veterinarian. Suitable dosage formulations and methods of administering the agents are known in the art. Route of administration can also be determined and method of determining the most effective route of administration are known to those of skill in the art and will vary with the composition used for treatment, the purpose of the treatment, the health condition or disease stage of the subject being treated, and target cell or tissue. Non-limiting examples of route of administration include oral administration, intraperitoneal, infusion, nasal administration, inhalation, injection, and topical application.

As used herein, the term "stable ungulate embryonic stem cell (ESC)" intends ungulate ESCs (e.g., bovine embryonic stem cells) that are pluripotent, easy to propagate using single cell dissociation by trypsin, and that maintained long-term stable morphology, karyotype, pluripotency markers expression, and epigenetic features typical of pluripotent cells. Moreover, with respect to bESCs, the cells displayed transcriptional and epigenetic characteristics of primed pluripotency which is evidenced by: 1) increased expression of DUSP6, ZIC3, DNMT3A/B ZIC2, OTX2, TET1, NCAM1, TET3, MYC, CD47, and 2) the presence of bivalent domains in HOXA1, FOXA2, GATA6, and TBX3 genes, and 3) the accumulation of H3K27me3-mark in HOXA9 and NKX-2 genes. In one aspect, the ESCs have been maintained in culture for over 50 weeks, or for over 60 weeks, or for over 70 weeks, or for over 80 weeks, or for over 90 weeds, or for over 100 weeks.

An ungulate is a hoofed animal, e.g., a bovine, an ovine, an equine, a pig, a giraffe, a camel, a deer, a hippopotamus, or a rhinoceros.

"Inactived feeder cells" are mitotically inactive mammalian cells, often obtained by treating cells with gama-irrradiation or incubation of cells in presence of mitomycin-C. Non-limiting examples of such include gamma irradiated mouse embryonic fibroblasts.

As used herein, "TeSR1" intends the medium as described by Sun et al. (2009) Proc Natl Acad Sci USA., September 15; 106(37):15720-5.

As used herein modified "TeSR1" refers to TeSR1 medium formulation modifications as described by Chen et al (2011) Nat. Methods, May; 8(5): 424-429. Published online 2011 Apr. 10.

Custom TeSR1 base medium refers to variations in the composition of TeSR1 or modified TeSR1 medium in which some components are left out (for example TGFβ).

N2B27 is a medium that comprises 25 mL of DMEM/F12 (available from ThermoFischer Scientific) plus N2 medium (protocol published by Cold Spring Harbor Protocol (2017) May 1, Vol. 5: pdb.rec086115, doi: 10.1101/pdb.rec096115), 25 mL of Neurobasal™ medium (neuronal cell basal medium) and B27 medium (a serum-free supplemental used for growth and long-term viability of hippocampal neurons) (each available from ThermoFischer Scientific, catalog number 21103049) and 50 μL of β-mercaptoethanol (100 mM). The medium without LIF and inhibitors is stored at 4° C. and used within one month.

DESCRIPTIVE EMBODIMENTS

Methods for Producing Stable Embryonic Stem Cell

Provided herein are methods for producing stable ungulate embryonic stem cells (ESCs), the methods comprising, or alternatively consisting essentially of, or yet further consisting of culturing an ungulate blastocyst cell or a pluripotent cell isolated from an ungulate embryo, in a cell culture media, the cell culture media comprising: (i) inactivated feeder cells; (ii) an effective amount of Fibroblast Growth Factor 2 (FGF2) or an equivalent thereof; and (iii) an effective amount of one or more of an inhibitor of Wnt signaling. In one aspect, the ungulate blastocyst, the pluripotent cell or the ESC is bovine or ovine. In a further aspect, the blastocyst cell, the pluripotent cell or ESC is detectable labeled.

The methods as disclosed herein use the disclosed compositions and culture conditions for the establishment of ungulate ESCs (e.g., bovine embryonic stem cells) that are pluripotent, easy to propagate using single cell dissociation by trypsin, and that maintained long-term stable morphology, karyotype, pluripotency markers expression, and epigenetic features typical of pluripotent cells. Moreover, with respect to bESCs, the cells displayed transcriptional and epigenetic characteristics of primed pluripotency which is evidenced by: 1) increased expression of DUSP6, ZIC3, DNMT3A/B ZIC2, OTX2, TET1, NCAM1, TET3, MYC, CD47, and 2) the presence of bivalent domains in HOXA1, FOXA2, GATA6, and TBX3 genes, and 3) the accumulation of H3K27me3-mark in HOXA9 and NKX-2 genes. Applicants also established that the primed CTFR-bESCs could integrate into the inner cell mass of bovine blastocysts and the efficacy of using long-term cultured bESCs as NT nuclei donors. The high efficient derivation of bovine ESCs can be harnessed for producing cattle and other ungulates with desired genetic value through genomic selection and/or genome editing, as well as for in vitro breeding schemes through germ cells derivation differentiation and in vitro fertilization. For example, high genetic value animals can be used to produce blastocyst that would be used for the derivation of CTFR-ESCs, and these cell lines are selected based on their genotypes as conventionally done in genomic selection approaches, the CTFR-bESC lines with highest genomic scores are selected and used to produce sperm and oocytes; which would then be used for in vitro fertilization and production of embryos. This second round of embryos are used to generate CTFR-ESCs, which would again be selected based on genomic merit, and used for another round of germ-cell generation, embryos and CTFR-bESCs. This approach allows rapid genetic improvements by significantly reducing generational interval and ensuring a high level of selection pressure. Furthermore, the possibility of culturing the cells in vitro indefinitely would also allow to introduce desired genetic variants by gene editing or traditional genetic engineering technologies at each generation, further accelerating genetic progress. Thus the methods lead to a significant reduction of the generational interval and accelerate genetic progress. Moreover, established ungulate ESCs represent a powerful platform for gaining novel insights into molecular features underpinning pluripotency program, enabling "omics" studies in pluripotent cells, e.g. whole genome transcriptional and epigenetic analysis, which typically require large number of cells with stable phenotype and are otherwise not possible with the limited number of the dynamic epiblast cells in early embryos.

The one or more inhibitors of Wnt signaling are selected from: IWR1, XAV-939, ICG-001, Wnt-059, LGK-974, LF3, CP21R7, NCB-0846, PNU-74654, Salinomycin, SKL2001, KY02111, IWP-2, IWP-L6, Wnt agonist 1, FH535, WIKI4, PRI-724, IQ-1, KYA1797K, 2,4-diamino-quinazoline, Ant1.4Br, Ant 1.4Cl, apicularen, bafilomycin, C59, ETC-159, G007-LK, G244-LM, IWR, Niclosamide, NSC668036, PKF115-584, pyrvinium, Quercetin, Shizokaol D, or BC2059 or a combination thereof. These are commercially available from vendors, for example Torcris Bioscience (tocris.com, last accessed on Jan. 11, 2018) or Santa Cruz Biotechnology, or available following methods provided in the technical literature. In one specific aspect, the inhibitor of Wnt signaling is IWR1 or an equivalent thereof.

In a further aspect of the method, the ungulate blastocyst cell or pluripotent cell is cultured in the absence of an effective amount of Transforming Growth Factor Beta (TGFβ) or an equivalent of TGFβ. In a further aspect, the TGFβ or an equivalent thereof is completely absent in the culture medium.

The steps of the method are not limited by any specific order. For example, one or more of the (i) inactivated feeder cells; (ii) the effective amount of Fibroblast Growth Factor 2 (FGF2) or an equivalent thereof; and (iii) the effective amount of the one or more inhibitors of Wnt signaling can be combined and then the blastocyst cell is added to the culture. Alternatively, in one aspect, the one or more of (i), (ii), or (iii) is provided in the cell culture media after to the addition of the ungulate blastocyst or the pluripotent cell. Alternatively, the one or both of (ii) the effective amount of Fibroblast Growth Factor 2 (FGF2) or an equivalent thereof; and (iii) the effective amount of the one or more inhibitors of Wnt signaling are added to the blastocyst cell or the pluripotent cell maintained on the inactivated feeder cells.

The amount of FGF2 or an equivalent thereof added to the culture conditions can be empirically determined; however non-limiting amounts range from about 5 ng/mL to about 50 ng/mL, or alternatively from about 10 ng/mL to about 100 ng/mL, or alternatively from about 10 ng/mL to about 50 ng/mL, or alternatively from about 10 ng/mL to about 40 ng/mL, or alternatively from about 10 ng/mL to about 30 ng/mL, each per mL of cell culture media. In one specific aspect, the effective amount of FGF2 or an equivalent thereof is about 20 ng/mL of cell culture media.

With respect to the one or more inhibitors of Wnt signaling, the effective amount can vary depending on the Wnt signaling inhibitor and can be empirically determined by those of skill in the art. Non-limiting amounts range from to a final concentration from about 0.1 mM to about 100 mM, after addition to the cell culture media. In another aspect, the effective amount of the one or more inhibitors of Wnt signaling is about 2.5 mM after addition to the cell culture media.

In a further aspect, the cell culture medium further comprises, or alternatively consists essentially of, or yet further consists of, an effective amount of a Rho-associated coiled-coil kinase (ROCK) inhibitor. Non-limiting examples of ROCK inhibitors include one or more of AS1892802, Fasudil hydrochloride, GSK 269962, GSK 429286, H1152, Glyclyl-H 1152, HA 1100, OXA 06, RKI 1447, SB 772077B, SR 3677, TC-S 7001, or Y-27632, or an equivalent of each thereof, or a combination thereof. In one aspect, the ROCK inhibitor is Y-27632 or an equivalent thereof. These are commercially available, e.g., Tocris Bioscience (tocris.com, last accessed on Jan. 11, 2018).

The effective amount of the ROCK inhibitor will depend on the specific inhibitor, and can be empirically determined using methods known in the art. Non-limiting examples of effective concentrations of ROCK inhibitors is about 1 μM to about 1000 μM, or from about 1 μM to about 100 μM, or from about 1 μM to about 50 μM, or from about 0.1 μM to about 100 μM, or about 0.1 μM to about 10 μM, each after addition to the cell culture media. In one aspect, the concentration of ROCK inhibitor is about 10 μM after addition to the cell culture media. In a further aspect, the ROCK inhibitor is Y-27632 or an equivalent thereof and the effective amount is about 10 μM after addition to the cell culture media.

In a further aspect, cell culture medium further comprises an effective amount of a low fatty acid BSA. In a yet further aspect, the cell culture medium is TeSR™1 basal medium. In a yet further aspect, the cell culture medium is modified TeSR™1 basal medium In one aspect, the inactivated feeder cells are murine embryonic fibroblasts, or alternatively the inactivated feeder cells are replaced by an organic extracellular matrix or feeder cell conditioned medium. Non-limiting examples of an organic matrix is Matrigel™ (a reconstituted basement membrane preparation) or vitronectin. In a yet further aspect, the inactivated feeder cells are replaced by an organic matrix, such as a Matrigel™ or vitronectin, and supplementation with an effective amount of Activin-A (commercially available from for example, R&D Systems (rndsystems.com/search?common_name=Activin%20A, last access on Jan. 18, 2018).

In some embodiments of the above methods, the blastocyst cell is an isolated inner cell mass cell. In a further aspect, the inner cell mass cell has been isolated by mechanical isolation or immunosurgery.

The cells can be cultured for an effective amount of time or passages, non-limiting examples of such include passaging the cells for at least 3 weeks or for at least 4 weeks, or for up to 10 weeks or more as noted herein.

In a further aspect, the ESCs prepared by the methods or can be genetically modified or the ungulate blastocyst cell or the pluripotent cell can be genetically modified. Thus the methods can further comprise modifying the ESC, or the pluripotent cell, or the blastocyst prior to culturing as noted above.

In one aspect, the ungulate embryo from which the pluripotent cells are isolated has been prepared by a method comprising nuclear transfer cloning or parthenogenetic activation. In another aspect, the embryo has been prepared by a method comprising natural or artificial insemination. In a further aspect, the blastocyst cell is isolated from a preimplantation embryo, optionally a morula or a cleavage stage embryo. In another aspect, the pluripotent cell of the embryo is isolated from the embryonic disk of a post-hatch embryo.

The ungulate embryonic cell or the pluripotent cell can be genetically modified prior to the culturing method or during the culturing method. Thus, the methods further comprise genetically modifying the blastocyst, or the pluripotent cell or ESC prior to culturing.

In any of the above methods, the blastocysts, or the pluripotent cell or ESCs can be detectable labeled prior to, during or subsequent to the culturing methods.

In a yet further aspect, the ESCs are isolated from the cell culture media after being cultured for an effective amount of time. In addition, one can also isolate one or more microvesicales or exosomes from the culture media.

Further provided are methods for performing genomic selection, the method comprising, consisting essentially of, or yet further consisting of: (i) screening ungulate ESCs that have been produced according to the method as prepared above for a preferred genotype; and (ii) selecting ungulate ESCs comprising the preferred genotype. Preferred genotypes could relate to particular breeding or other agricultural traits, e.g., high milk production for bovines, for example or certain traits for meat production or quality, e.g., fat or protein content.

One can modify the ungulate embryo, by any appropriate method, e.g., comprising establishing an embryo from a nuclear transfer process wherein the ungulate ESC is inserted into an enucleated ungulate oocyte.

Further provided is a method of genetically modifying an ungulate, the method comprising, or alternatively consisting essentially of, or yet further consisting of, (a) establishing an embryo from a nuclear transfer process wherein the ungulate ESC as disclosed herein is inserted into an enucleated ungulate oocyte, and (b) implanting the embryo into a non-human recipient host. In a further aspect, the embryo is gestated in the recipient host. The resulting non-human animal and its offspring from the implanted embryo is further disclosed herein. In a yet further aspect, the method can further comprise introducing the ungulate ESC to a genetically modified embryo or an embryo produced by nuclear transfer cloning.

Yet further provided is a method of creating a chimeric non-human animal, the method comprising, or alternatively consisting essentially of, or yet further consisting of: (a)

generation of ungulate ESC; (b) introduction of ungulate ESC into a preimplantation embryo; and (c) transfer of embryo to a non-human recipient. Yet further provided is the non-human animal prepared by the method and the offspring from the ESC.

Yet further provided is a method for creating ungulate germ cells (sperm and oocytes) from ungulate ESC, the method comprising, or alternatively consisting essentially of, or yet further consisting of: (a) generating ungulate ESC; (b) in vitro differentiation of the ungulate ESC to germ cells by addition/subtraction of growth factors and/or co-culture with somatic cells; (or) (c) transplantation of the ungulate ESC or intermediate differentiated cells into an non-human animal for generation of germ cells. In one aspect, the ungulate ESC are transplanted to a germline-deficient non-human embryo. In a further aspect, the ungulate ESC are transplanted to a non-bovine animal or a bovine animal. Yet further provided are the non-human animals prepared by these methods, as well the offspring from the transplanted ESC.

Isolated Cells, Exomes and Compositions

Further provided are compositions, cells, microvesicles, exosomes and non-human animals as well as their offspring prepared by the above methods. In one aspect, provided herein is the ungulate ESC produced according to the methods as well as populations of the ungulate ESCs produced by the methods. The populations can be homogenous with respect to a desired phenotype or genotype, wherein at least 70%, or 80%, or 85%, or 90%, or 95%, or 97% or 98% of the cells are of the desired phenotype or genotype. The cells and populations can be detectably labeled.

This disclosure also provides a microvesicle or exosome isolated from the cells produced by these methods as well as populations of the microvesicle or exosomes produced by the cells produced by methods of this disclosure. The populations can be homogenous with respect to a desired phenotype or genotype, wherein at least 70%, or 80%, or 85%, or 90%, or 95%, or 97% or 98% of the cells are of the desired phenotype or genotype. The microvesicles, exosomes or populations can be detectably labeled.

In a further aspect, the compositions further comprise a carrier such as a pharmaceutically acceptable carrier. In a further aspect, the compositions also comprise a cryopreservative or a preservative.

Modes for Carrying Out the Disclosure

Applicants have discovered that under specific culture conditions. Embryonic stem cells (ESCs) can be captured and expanded from the inner cell mass (ICM) of blastocyst stage embryos. Once stabilized, ESCs can proliferate unlimitedly in culture while remaining pluripotent—the ability to generate a multitude of cell types and tissues.

Producing stable ungulate ESCs such as bovine ESCs will not only enrich the understanding of pluripotency and early development in livestock species, but also facilitate agricultural- and biotechnological-related applications such as production of genetically superior animals by genomic selection and/or genome editing and broadening the utility of transgenic animal bioreactors.

In addition to the pluripotent ESCs derived from pre-implantation embryos, epiblast stem cells (EpiSCs) can be derived from the epiblast of post-implantation embryos exhibiting also some of the hallmarks of pluripotency; however, they are inefficient in generating blastocyst chimeras as a result of their poor survival in the blastocyst environment. ESCs and EpiSCs have distinct molecular characteristics and embody different pluripotent states termed "naïve" and "primed", respectively. Although both are sourced from pre-implantation stage embryos, mouse ESCs are the gold standard of naïve pluripotency while human ESCs more resemble mouse EpiSCs and exist in the more advanced primed pluripotent state. Both human ESCs and mouse EpiSCs are notorious for their poor single cell clonality, which is undesirable for gene editing. In addition, their derivation efficiencies vary. Recently, a new culture condition was used to obtain a novel type of primed EpiSCs that share molecular features with gastrula stage epiblast and was designated as region-selective pluripotent stem cells (rsPSCs) due to their unique property to preferentially engraft to the posterior part of the gastrula stage mouse epiblast. Remarkably, the rsPSC condition, based on a simple serum free culture with Fibroblast Growth Factor 2 (FGF2) and an inhibitor of the canonical Wnt-β-catenin signaling pathway (IWR1), allowed for clonal expansion of both human ESCs and mouse EpiSCs in vitro and perfect EpiSC derivation efficiency from both pre- and post-implantation murine embryos.

In this study, Applicants employed the rsPSC culture condition for the establishment of bovine embryonic stem cells and that derive, with high efficiency, bESCs that are pluripotent, easy to propagate using single cell dissociation by trypsin, and that maintained long-term stable morphology, karyotype, pluripotency markers expression, and epigenetic features typical of pluripotent cells. Moreover, bESCs displayed transcriptional and epigenetic characteristics of primed pluripotency which is evidenced by: 1) increased expression of DUSP6, ZIC3, DNMT3A/B ZIC2, OTX2, TET1, NCAM1, TET3, MYC, CD47, and 2) the presence of bivalent domains in HOXA1, FOXA2, GATA6, and TBX3 genes, and 3) the accumulation of H3K27me3-mark in HOXA9 and NKX-2 genes. Surprisingly, however, the primed CTFR-bESCs could integrate into the inner cell mass of bovine blastocysts. In addition, Applicants demonstrated the efficacy of using long-term cultured bESCs as NT nuclei donors. The high efficient derivation of bovine ESCs can be harnessed for producing cattle with desired genetic value through genomic selection and/or genome editing, as well as for in vitro breeding schemes through germ cells derivation differentiation and in vitro fertilization. For example, high genetic value animals could be used to produce blastocyst that would be used for the derivation of CTFR-bESCs, and these cell lines could be selected based on their genotypes as conventionally done in genomic selection approaches, the CTFR-bESC lines with highest genomic scores would be selected and used to produce sperm and oocytes; which would then be used for in vitro fertilization and production of embryos. This second round of embryos would again be used to generate CTFR-bESCs, which would again be selected based on genomic merit, and used for another round of germ-cell generation, embryos and CTFR-bESCs. This approach would allow rapid genetic improvements by significantly reducing generational interval and ensuring a high level of selection pressure. Furthermore, the possibility of culturing the cells in vitro indefinitely would also allow to introduce desired genetic variants by gene editing or traditional genetic engineering technologies at each generation, further accelerating genetic progress. These applications would lead to a significant reduction of the generational interval and accelerate genetic progress. Moreover, established bESCs represent a powerful platform for gaining novel insights into molecular features underpinning bovine pluripotency program, enabling "omics" studies in pluripotent cells, e.g. whole genome transcriptional and epigenetic analysis, which typically require large number of cells with stable phenotype and are otherwise not possible with the limited number of the dynamic epiblast cells in early embryos.

Embryonic stem cells (ESCs) are derived from the inner cell mass of pre-implantation blastocysts. From an agricultural and biomedical perspectives, the derivation of stable ESCs from domestic ungulates is important for genomic testing and selection, genetic engineering, and providing an experimental tool for studying human diseases. Cattle are one of the most important domestic ungulates that are commonly used for food and bioreactors. To date, however, it remains a challenge to produce stable pluripotent bovine ESC lines. Employing a culture system containing fibroblast growth factor 2 and an inhibitor of the canonical Wnt-signaling pathway, Applicants produced pluripotent bovine ESCs (bESCs) with stable morphology, karyotype, pluripotency marker expression, and epigenetic profiles. bESCs were derived with high efficiency (100% in optimal conditions), were simple to propagate (by enzymatic treatment, such as trypsin and TrypLE), and were fast to establish (3 to 4 weeks). Also, when used as donors for nuclear transfer, bESCs produced normal blastocysts rates opening the possibility to use them for genomic selection, genome editing, and production of cattle with high-genetic value.

The derivation of stable ESCs from domestic ungulates is important for genomic testing and selection, genetic engineering, and providing an experimental tool for studying human diseases. ESCs have been derived and extensively studied in rodents and primates; however, it has been challenging to derive and propagate stable ESCs. Here, Applicants report that stable bovine ESC can be efficiently derived in a novel culture condition based on Wnt-pathway inhibition. These well-characterized ESC lines will not only enrich our understanding of pluripotency programs in the ungulate species, but also provide a useful resource for the creation of transgenic large animal models of human diseases.

The following example are provided to exemplify the aforementioned concepts and disclosures.

EXAMPLE 1

Figure 1B:
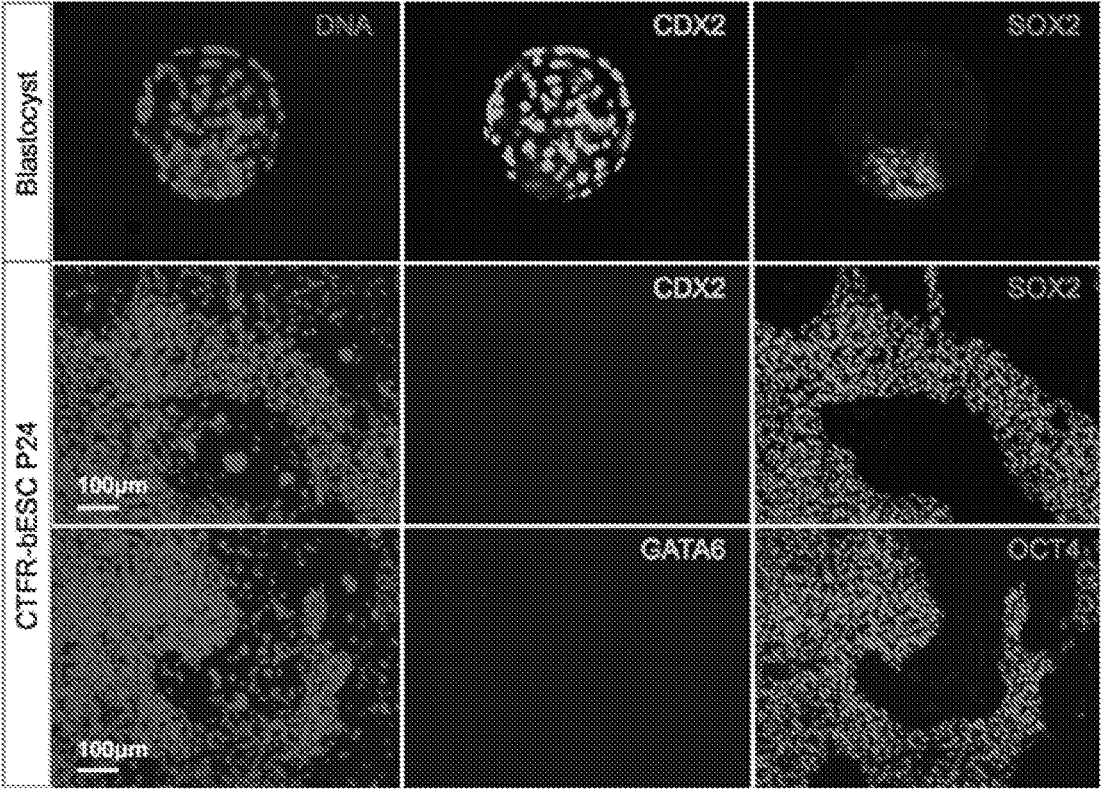
Figure 2B:
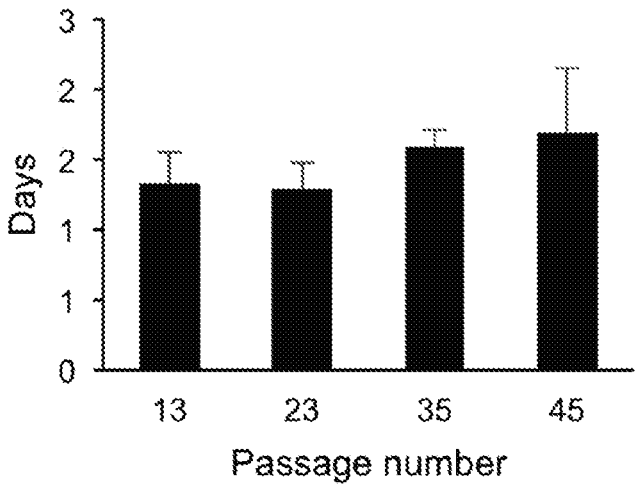

CTFR Medium Supports Derivation and Long-Term Culture of Pluripotent bESCs bESCs were derived, propagated, cultured, and subjected to several rounds of freezing and thawing in serum free Custom TeSR1 base medium (without growth factors) supplemented with FGF2 and IWR1 (herein referred to as "CTFR") conditions. Cell lines could be established by the end of week 3 after ICM/embryo plating and remained unchanged for more than 50 passages (FIG. 1). Unlike human ESCs and mouse EpiSCs, CTFR-bESC did not show round colony morphology with clearly defined edge, but rather grew tightly attached to each other as an interconnected cellular web that was clearly delimited from the feeder layer (FIG. 1A). CTFR-bESCs were positive for alkaline phosphatase (AP) staining (FIG. IA). To assess genetic stability of the CTFR-bESCs after long-term culture, applicants performed karyotyping assay in two different cell lines at passage 34. The results showed a normal chromosome content (n=60) in more than 70% of the examined metaphase cells (FIG. 2A). Immunofluorescence-analysis (IF) revealed that long-term cultured CTFR-bESCs expressed the pluripotency markers SOX2 and OCT4 but not the trophectoderm (TE) and primitive endoderm (PE) markers CDX2 and GATA6, respectively (FIG. 1B). IF assays of bovine blastocysts (BLs) showed that SOX2 positive cells were exclusively found in the ICM while CDX2 signal was limited to the TE cells (FIG. 1B). A SOX2 positive and CDX2 negative IF staining pattern was consistently produced in CTFR-bESCs from passage 4 onwards, indicating that CTFR culture favored proliferation of ICM over TE cells.

Addition of canonical WNT inhibitor is critical for the successful derivation and propagation of bovine ESCs, since withdrawal of IWR1 from the culture media resulted in loss of pluripotency marker expression (FIG. 3). In addition, no bESC line could be established if IWR1 was not present in the culture medium.

Figure 2C:
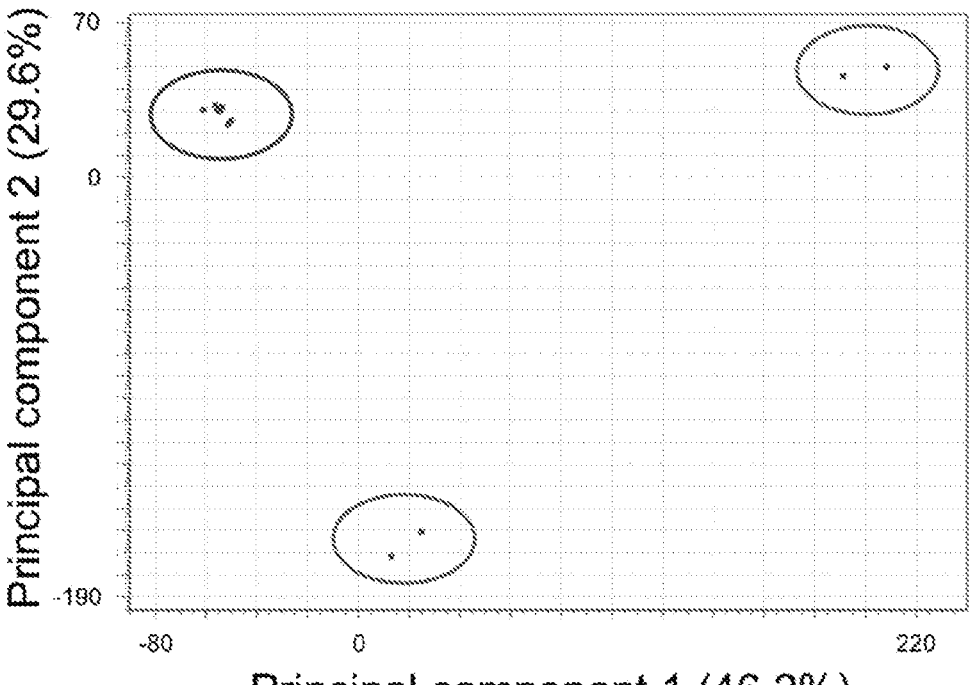
Figure 2D:
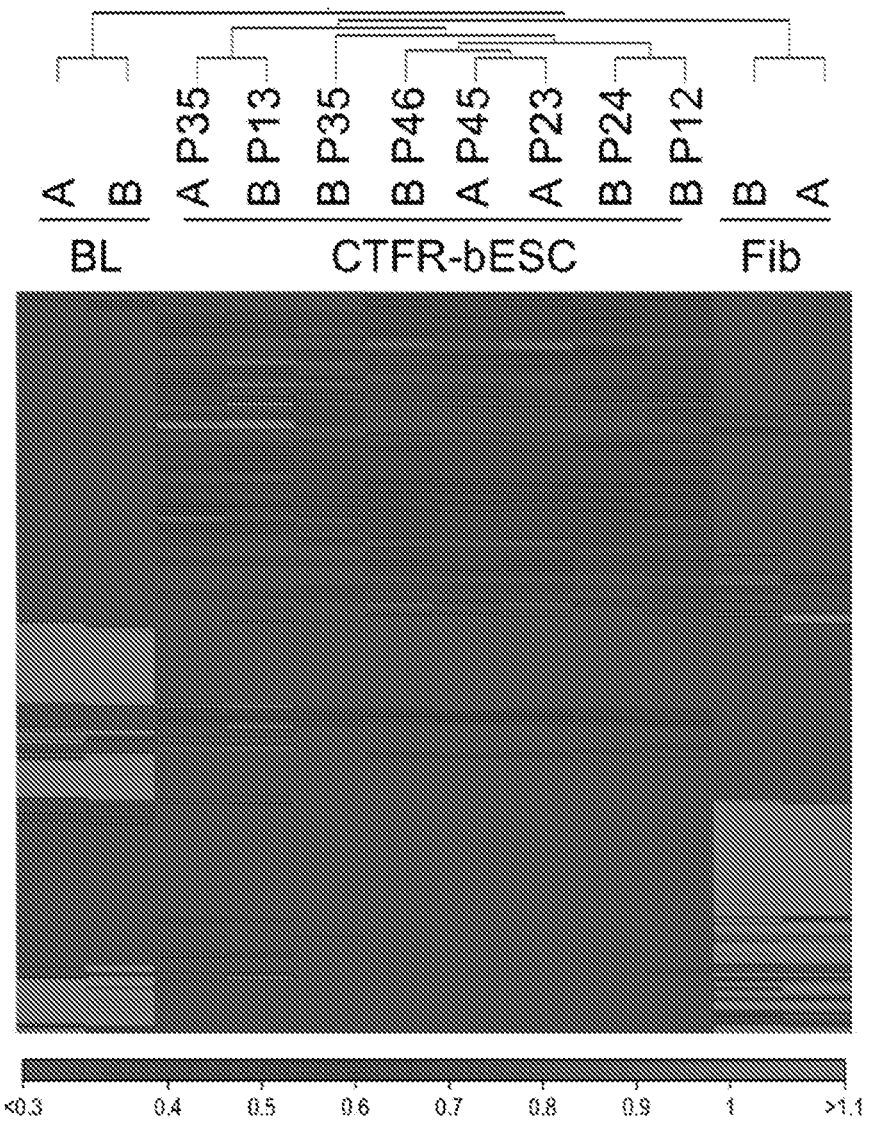
Figures 2E, 2F:
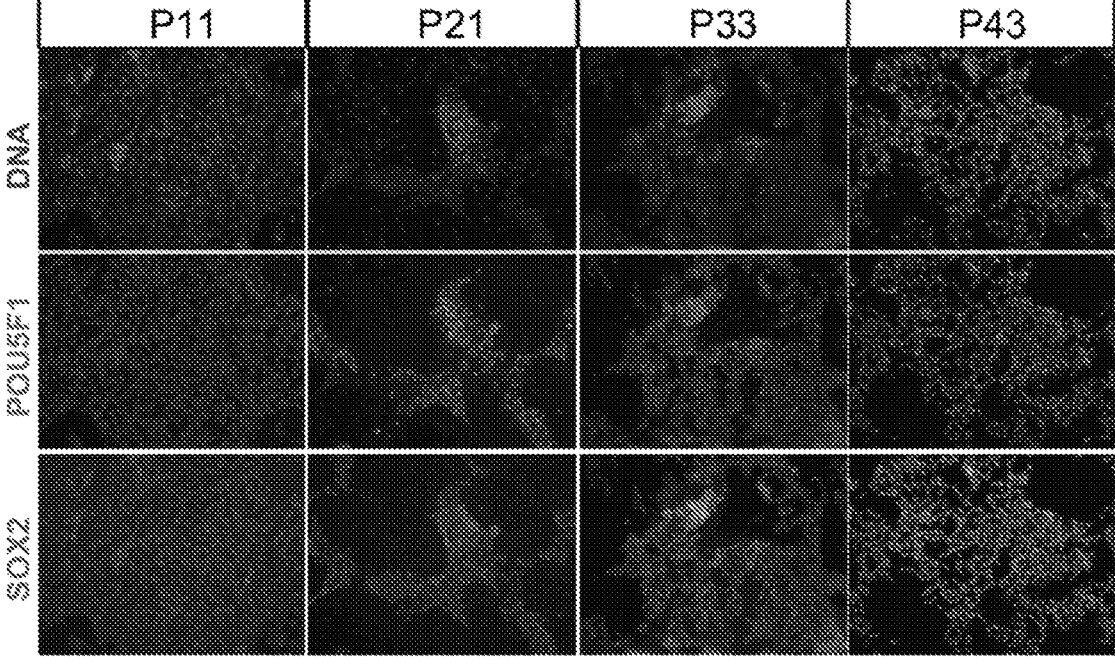

Applicants also performed transcriptome analysis by RNA-sequencing (RNA-seq) using two independently established and long-term cultured CTFR-bESC lines, whole bovine blastocysts and bovine fibroblasts. The analysis showed that ICM markers, POU5F1 (a.k.a. OCT4), SOX2, NANOG, LIN28B, DNMT1B, UTF1, and SALL4, were expressed (RPKM≥0.4) in CTFR-bESC lines and bovine blastocysts, but not (RPKM<0.4) in bovine fibroblasts (control) (FIG. 1C). On the other hand, both TE and PE markers were found absent in CTFR-bESC lines but expressed in the blastocysts. Of note is that CTFR-bESCs' transcriptome profile remained stable even after long term culture (FIGS. 2C, 2D, and 2E). These results indicate that the expression profile of CTFR-bESCs was more similar to the pluripotent ICM than TE or fibroblast cells.

Figure 2G:
Figure 2H:
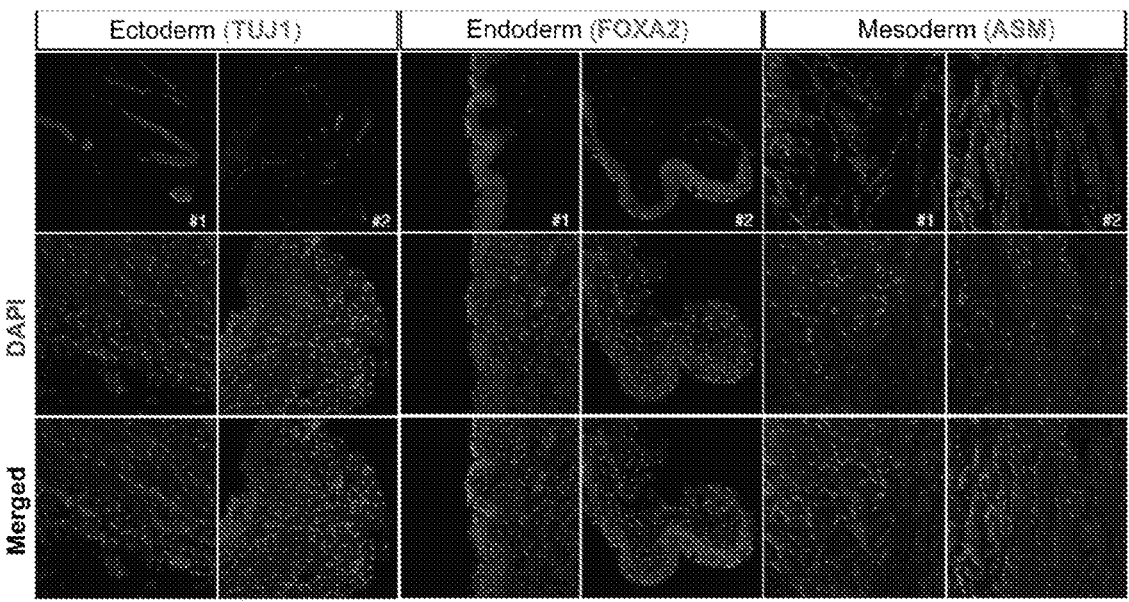

Applicant also performed intramuscular injection of two CTFR-bESC lines into immunodeficient NOD SCID mice for teratoma formation assay to evaluate whether established CTFR-bESC lines are pluripotent. Both cell lines were able to form teratomas (FIGS. 2G and 2H) containing tissues from all three primary germ layers: ectoderm, mesoderm, and endoderm as evidenced by H&E staining (FIG. 1D) and IF analysis: ectoderm (TUJ1), endoderm (FOXA2), and mesoderm (ASM) (FIG. 2H). These results indicate that CTFR-bESCs maintained pluripotency after extended in vitro culture.

Histone Methylation Landscape of CTFR-bESCs

Figures 4C, 5A:
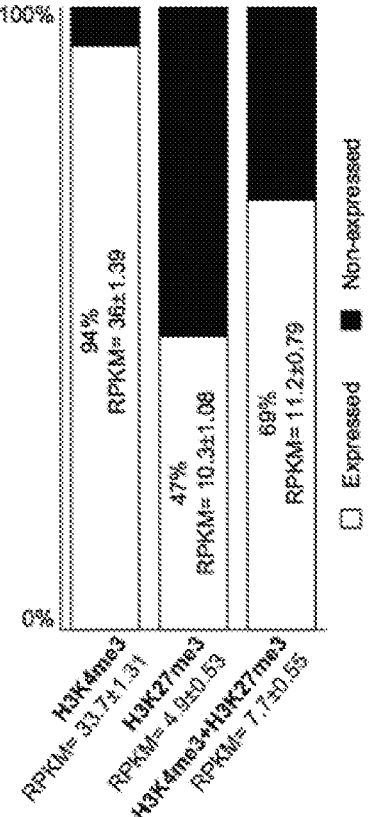

Lack of culture conditions that supports long-term propagation of pluripotent ESCs has impeded our molecular understanding of pluripotency in large livestock species. By taking advantage of the stable pluripotent CTFR-bESC lines, Applicants next examined the global distribution of H3K4me3 and H3K27me3 marks in cultured CTFR-bESCs to gain insights into the epigenetic regulation of bovine pluripotency program. To this end, a low-input ChIP-seq protocol was implemented. An average of 31 million uniquely mapped reads were used for peak calling (FIG. 4A) which resulted in 8,816, 2,553, and 3,886 genes associated only with H3K4me3, H3K27me3, or both (bivalent domains), respectively. Transcriptome analysis by RNA-seq showed that most of the H3K4me3-only genes were expressed (94%; RPKM≥0.4), while 47% and 64% were expressed in H3K27me3-only and bivalent-genes respectively (FIG. 5A). Notably, gene expression levels were higher for H3K4me3-only genes than in H3K27me3-only and bivalent-genes (average RPKM=34, 5 and 8, respectively).

Figure 5B:
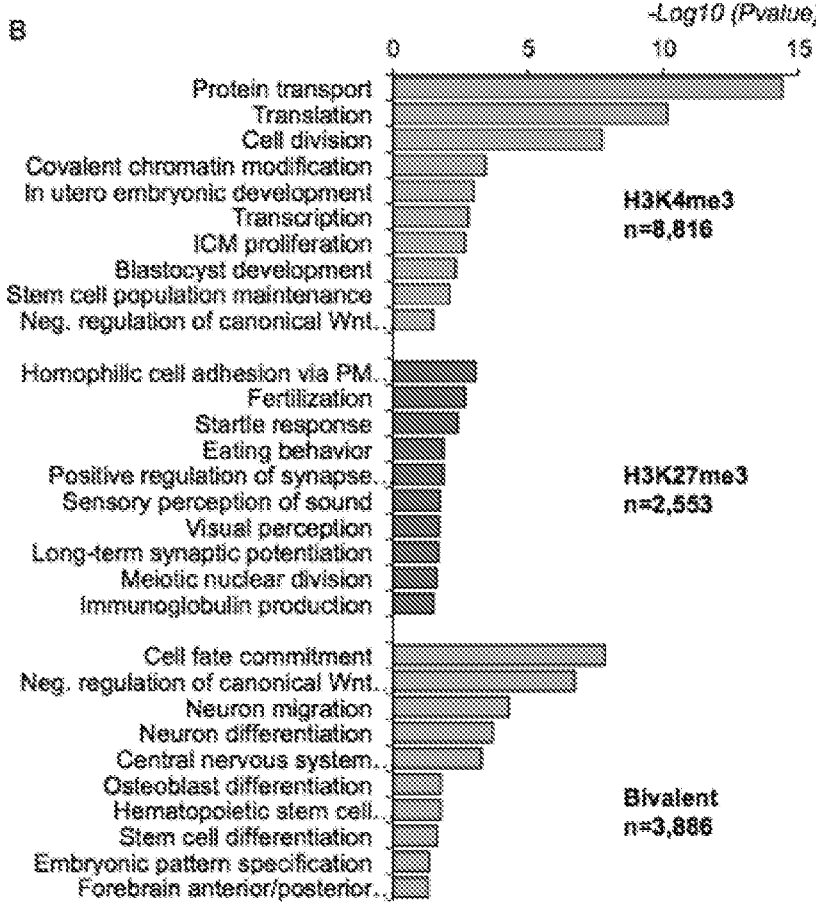

Gene ontology (GO) terms associated with genes exclusively marked by H3K4me3 included not only housekeeping cellular functions such as protein transport, cell division, transcription, and translation, but also specific pluripotency-related functions including inner cell mass proliferation, stem cell population maintenance, and blastocyst development (FIG. 5B). Also, consistent with the use of a small molecule Wnt-inhibitor (IWR1) for CTFR-bESC culture, a noteworthy enriched term was the negative regulation of the canonical Wnt-signaling pathway. Enriched GO terms of H3K27me3-only genes related to specific functions that are generally silenced in PSCs such as fertilization, startle response, immunoglobulin production, and visual perception. Lastly, enriched GO terms for bivalent genes were mainly related to cell fate decisions e.g. cell fate commitment, neuron migration and differentiation, central nervous system development, and stem cell differentiation (FIG. 5B).

Figure 5C:
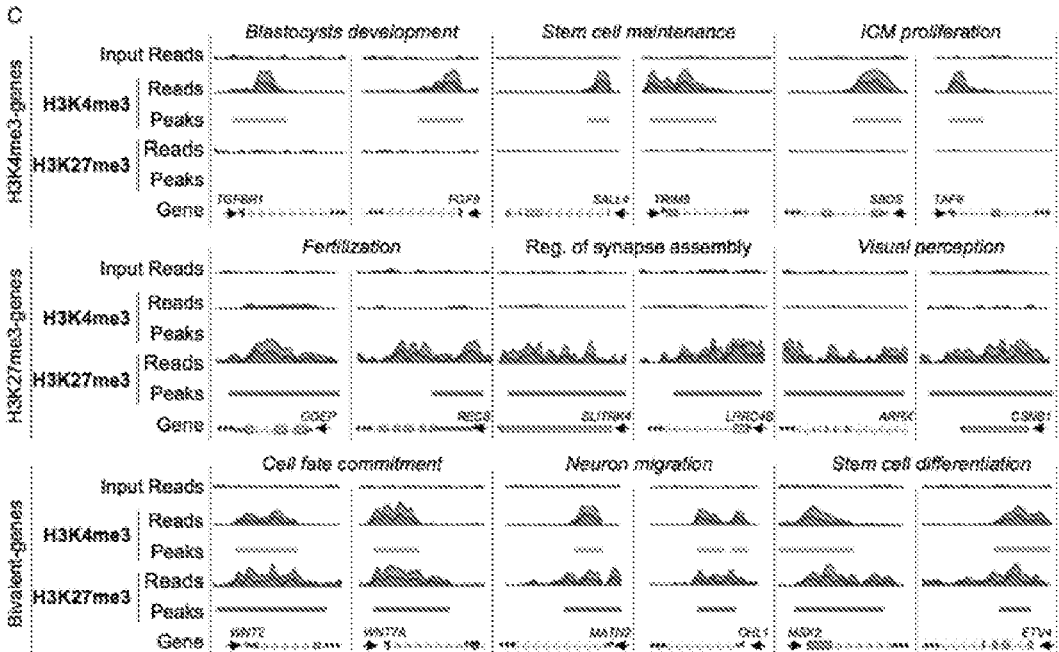

Visual assessment of genes associated with three selected GO terms for H3K4me3-, H3K27me3- or bivalent-genes are shown in FIG. 5C. Applicants found that genes containing the H3K4me3-mark presented well-defined peaks in their promoter regions, while H3K27me3-genes presented broader peaks (some in the promoter region but most of them covered much of their gene bodies). Bivalent genes showed co-localization of H3K4me3 and H3K27me3 marks near their promoter regions. Notably, for bivalent genes the H3K27me3 mark was more restricted to the TSS than H3K27me3-only genes, and showed peak shapes similar to H3K4me3 (FIG. 5C).

Although mouse and human ESCs exhibit distinct molecular characteristics, they do share some common transcriptional and epigenetic features characteristic of pluripotent cells. Applicants compared lists of genes that are known to harbor H3K4me3, H3K27me3, or bivalent domains in human and mouse ESCs with that of CTFR-bESCs and found that 62% (n=4,898) of H3K4me3-only bovine genes also contained that mark in human and/or mouse ESCs (FIGS. 4B and 4C). Most of these genes were shared by both species (33%, n=2,563), while a higher number of genes were shared with human ESC (23%, n=1822) than mouse ESCs (6% n=513). Forty-four percent of the bovine bivalent genes were also shared by mouse and/or human ESCs, among which half was shared by all three species (n=757). Similarly, bovine bivalent-genes showed more similarity to those of human ESCs than mouse ESCs (13%, n=447 and 9%, n=317, respectively). Interestingly, only 4% of the H3K27me3-only bovine genes (n=1,697) were shared with those in the other two species. This low level of overlap was likely due to low number of H3K27me3-genes in mouse (n=137) and human ESCs (n=424). Overall, these results suggest that bESCs have an epigenetic landscape similar to PSCs from other mammalian species, further confirming their pluripotent status.

Figures 6A, 6B:
FIGS. 6A-6D: CTFR-bESCs show molecular signatures characteristic of primed pluripotency.

CTFR-bESCs Display Transcriptional and Epigenetic Features Characteristic of the Primed Pluripotent State To investigate the pluripotency state of CTFR-bESCs, Applicants analyzed the expression of typical naïve and primed pluripotency markers identified in mouse and human ESC studies. Most of the examined primed pluripotency markers were expressed (RPKM≥0.4) in the CTFR-bESCs (19/22, 86%) while fewer of the naïve markers did (14/22, 64%). Also, the average RPKM values of all the analyzed markers were higher for the primed—than the naïve-pluripotency marker genes (RPKM=25±8.4 and RPKM=17±13, respectively) (FIG. 6A).

Figure 6C:

It has been shown that the sole presence of H3K4me3 peak in the promoter region of OCT4, SOX2, SALL4, and NANOG genes are characteristic of both naïve and primed pluripotency. Consistent with mouse and human, CTFR-bESCs also showed sharp H3K4me3 peaks at the promoter regions of these genes, revealing conserved epigenetic features of core pluripotency genes (FIG. 6B). Applicants next assessed the presence of H3K4me3- and H3K27me3-marks on CTFR-bESCs-genes that display differential histone methylation landscape in naïve and primed pluripotency states in mouse and human species. It was observed that, for all the examined genes, the epigenetic signatures in CTFR-bESCs coincided with a primed pluripotency state, with bivalent domains present in HOXA1, FOXA2, GATA6, and TBX3 genes and accumulation of H3K27me3-mark in HOXA9 and NKX-2 genes (FIG. 6C).

Taken together, these results show that important epigenetic features, such as the presence of the H3K4me3 marks at the TSS of key pluripotency genes are shared across distant mammalian species, and that CTFR-bESCs represent a primed type of pluripotency.

CTFR-bESCs Can Integrate into the ICM of Bovine Blastocysts In-Vitro

Figure 6D:
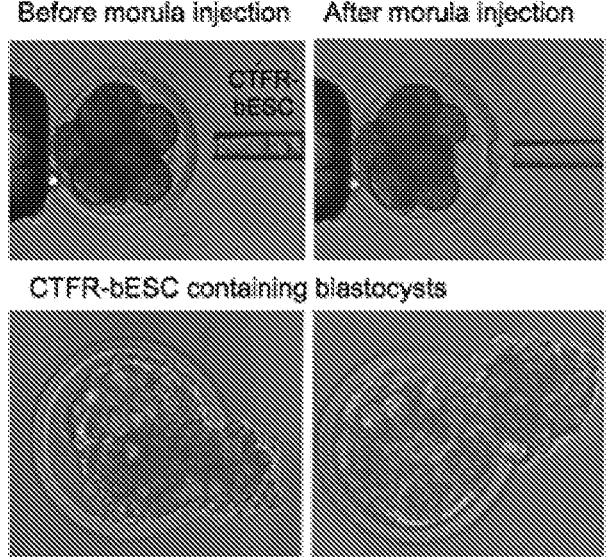

Primed mouse EpiSCs display poor survival and are inefficient in colonizing murine ICMs. Applicants examined the ability of CTFR-bESCs to integrate into pre-implantation bovine embryos. CTFR-bESCs were first labeled with a green fluorescent protein (GFP) marker and injected into day 5 bovine morulas. After additional 3 days in culture, first with 1:1 mixture of CTFR and embryo culture media for 20 hours followed by embryo culture medium alone, applicants detected many GFP-bESCs in day 8 blastocyst embryos, indicating the capacity of CTFR-bESCs to survive and proliferate inside the bovine embryo (FIG. 6D).

CTFR-bESCs Derivation is Highly Efficient

Figure 8A:
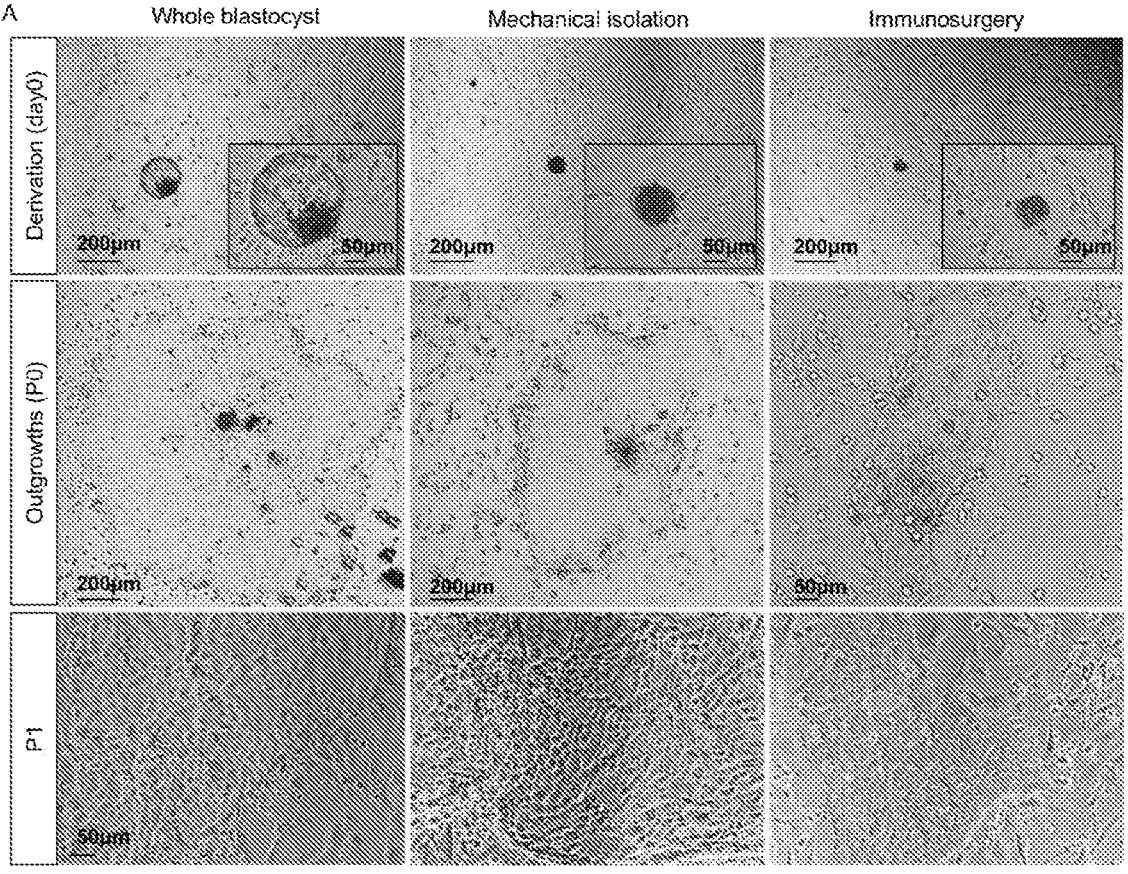
FIGS. 8A-8C. CTFR-bESCs can be derived utilizing different plating methods and be used to produce NT-embryos.
Figure 8B:
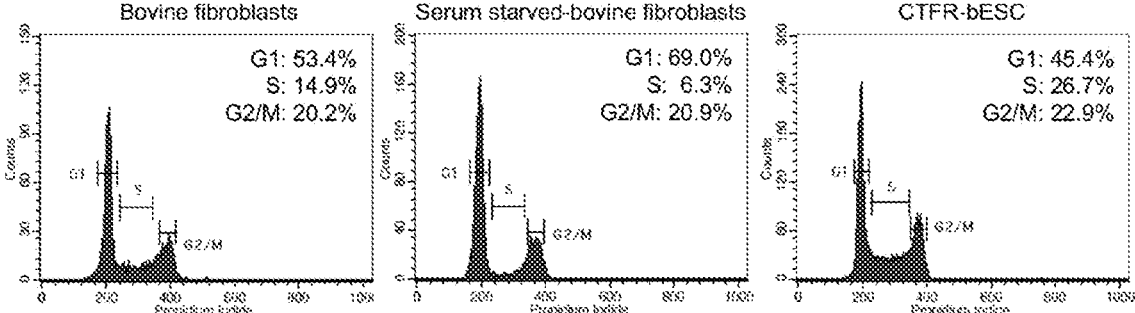

CTFR-bESCs derivation efficiency was measured as the percentage of embryos successfully establishing a CTFR-bESC line at passage 3 over the total number of embryos seeded. To optimize the CTFR-bESCs derivation efficiency, Applicants evaluated three different plating methods: whole blastocyst, mechanical isolation of the ICM by microdissection, and isolation of the ICM by immunosurgery. No difference was found in derivation efficiency among all three methods and the efficiency was comparable or even higher than what has been reported for the derivation of mouse ESCs (FIG. 7A). The initial outgrowths from the three methods were slightly different. The immunosurgery-derived outgrowths were smaller and more homogeneous in cell morphology than those from the other two methods. However, by the end of the second week, cells showed the same morphology regardless of the derivation methods (FIG. 8) These results indicate that even with simple whole-blastocyst plating, CTFR-bESCs could be derived at high efficiency with homogeneous cell morphology within a short period of time.

Applicants next derived CTFR-bESCs from different embryo sources and examined whether the embryo source could affect the derivation efficiency. Applicants found that when using OPU-IVF-derived embryos of the Holstein and Jersey breeds derivation efficiency was 100% and 64%, respectively; while when using embryos produced by IVF of oocytes aspirated from slaughterhouse-derived ovaries (IVM-IVF) the efficiency was 52%. SCNT-derived embryos produced CTFR-bESCs with 75% efficiency. Overall, these results show that CTFR-bESCs can be efficiently produced from different embryo sources (FIG. 7A).

CTFR-bESCs Can be Used as Nuclear Donors for NT-Cloning

Figure 8C:

A potential application of CTFR-bESCs in cattle is for genomic selection followed by production of NT-derived animals (FIG. 7B). To this end the possibility of generating NT-embryos using CTFR-bESCs (obtained from different embryo sources) was tested and found that all of them were able to produce NT-blastocysts at efficiencies ranging from 10 to 20%, a slightly lower blastocyst formation rate than control fibroblasts (28%) (FIG. 4C). A possible explanation for the reduced blastocyst development of embryos cloned from CTFR-bESCs is that these cells were not synchronized in G1/G0 stage of the cell cycle before NT. Upon FACS analysis of DNA content in bESC and fibroblasts subjected to serum-starvation (FIG. 8B) Applicants noticed that bESC cultures had only half as many cells in G1 compared to fibroblasts, with a higher percentage of cells in S phase, a cell cycle stage that is incompatible with NT embryo development. Finally, the CTFR-bESC-NT embryos can be used to derive secondary CTFR-bESCs that displayed SOX2 and OCT4 IF-staining patterns identical to the original cells (FIG. 8C).

CTFR-bESCs Can be Cultured in a Feeder-Free Condition

Figure 9:
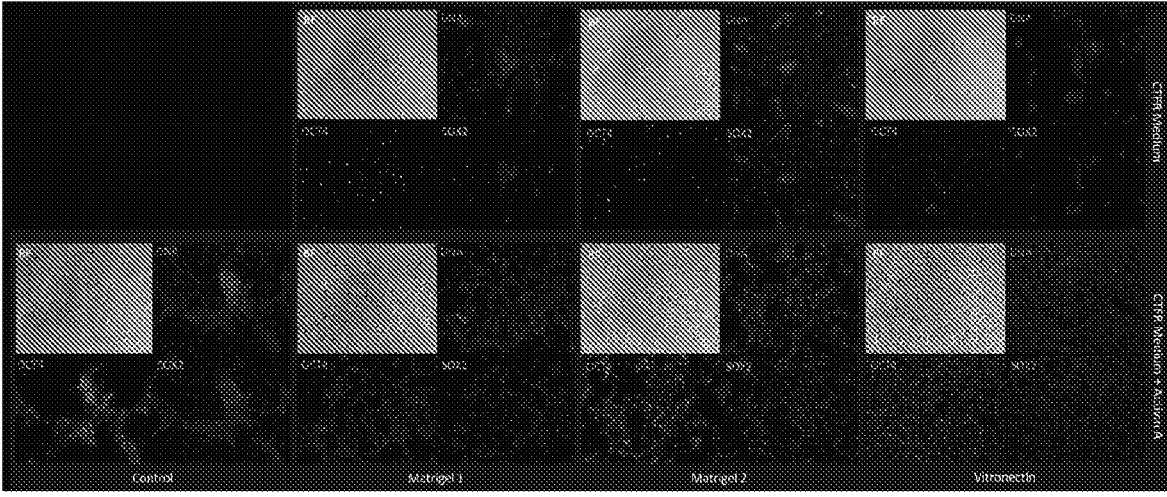
FIG. 9. CTFR-bESCs can be cultured in feeder-free conditions. Brightfield images and immunostaining for pluripotency markers OCT4 and SOX2 of CTFR-bESCs cultured for four passages on mouse embryonic fibroblast (MEF) feeder (Control) or different extracellular matrices (Matrigel or Vitronectin) conditions, with or without the supplementation of Activin-A (10 ng/mL). Control: inactivated MEFs. Only cells cultured in matrigel and vitronectin and supplemented with Activin-A maintained expression of pluripotency markers and a morphology consistent with CTFR-bESC.

Culturing CTFR-bESCs in absence of feeder cells lead to cellular differentiation after a few passages. On the other hand, culturing CTFR-bESCs on an organic matrix such as Matrigel or Vitronectin and supplementing the culture medium with Activin-A allowed the propagation of the cells for multiple passages while maintaining expression of pluripotency markers (FIG. 9)

CTFR Condition Can be Used to Derive Stable Pluripotent ESC from Sheep Embryos

Figures 10A, 10B:
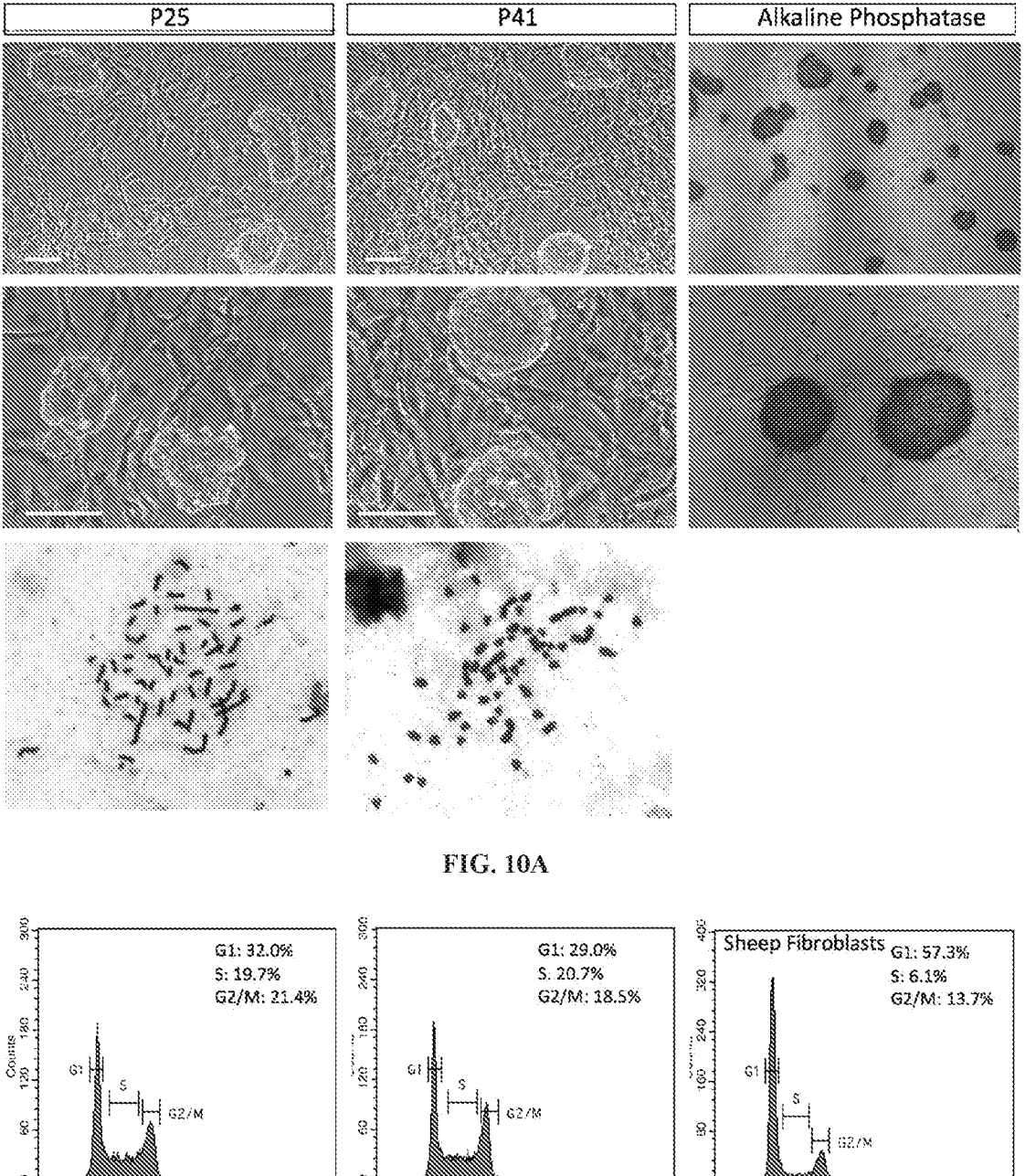
FIGS. 10A-10D. CTFR conditions can be used to derive stable pluripotent ESC from sheep pre-implantation embryos.
Figure 10C:
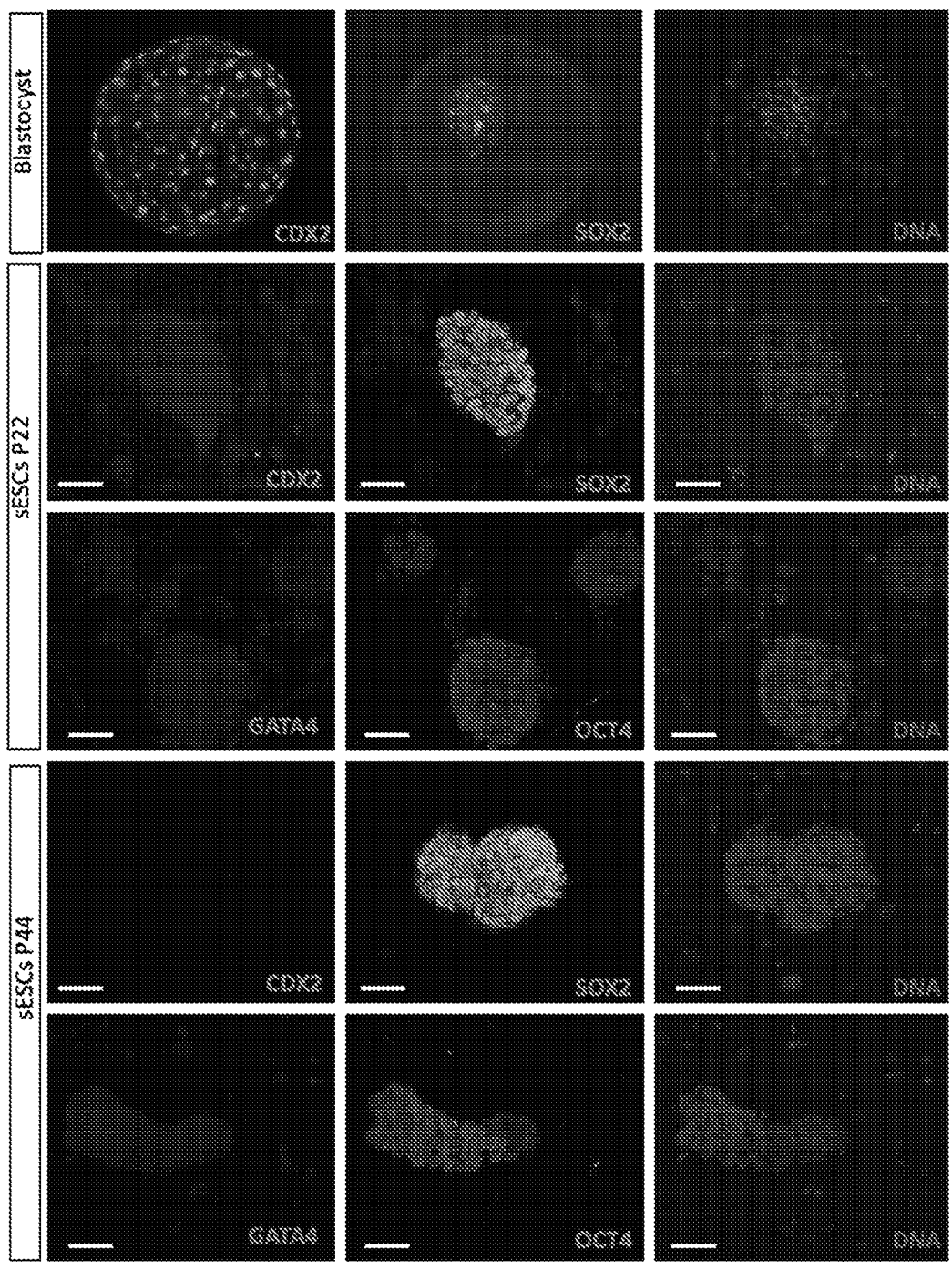
Figure 10D:
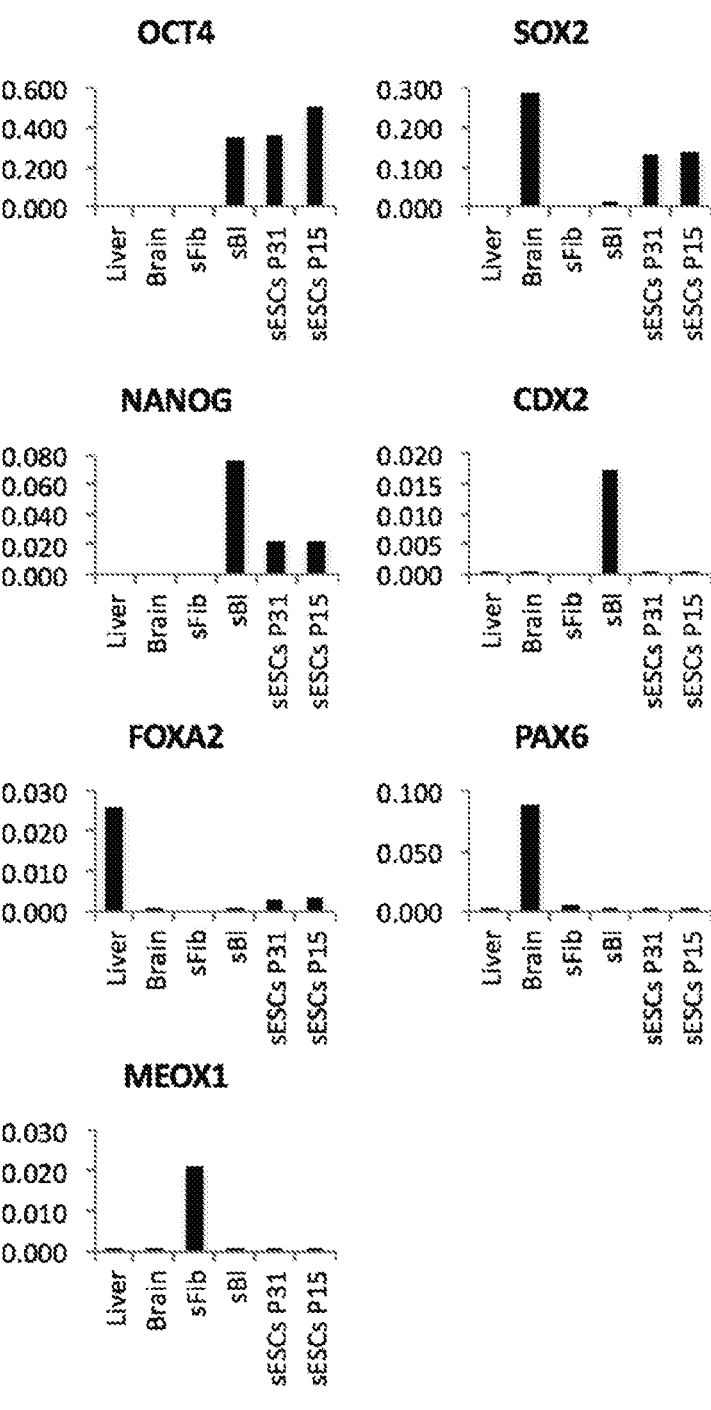
Figures 11A, 11B:
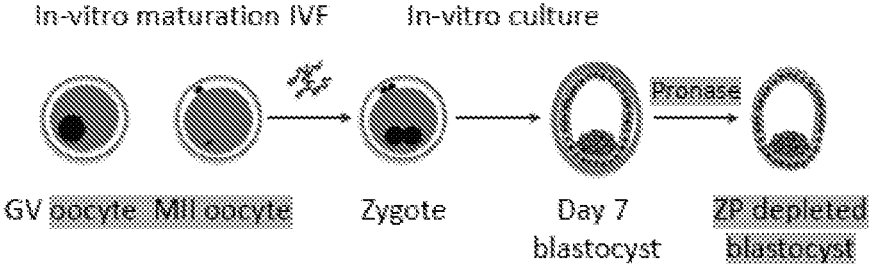
FIGS. 11A-11C are schematics showing embryo production protocol (FIG. 11A), culture conditions (FIG. 11B), and a comparison of derivation methods and protocol (FIG. 11C).
Figure 11C:
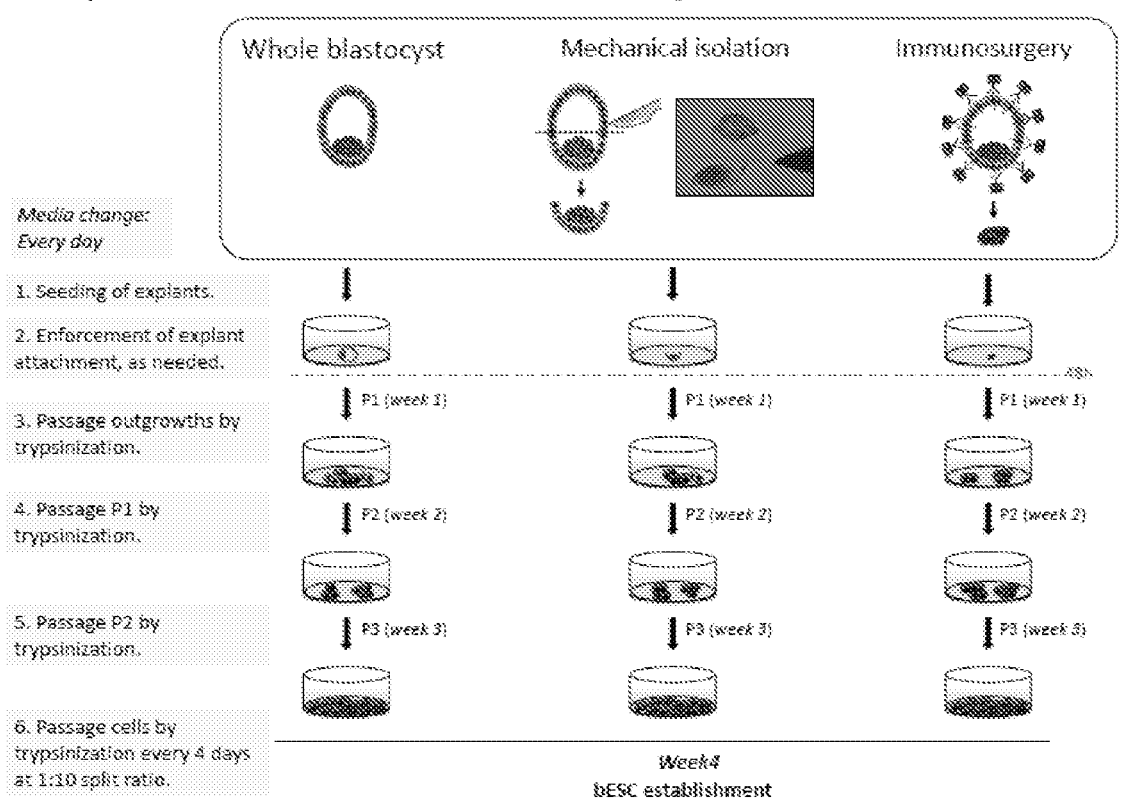

Using the same CTFR condition described for the derivation and culture of bovine ESC, ESC from sheep embryos were also successfully derived. The ovine ESC (oESC) presented round colony morphology and were stable after over 40 passages while maintaining alkalin phosphatase activity (a marker for pluripotent cells) and normal ploidy (FIG. 10A). CTFR-oESC presented a cell cycle profile characteristic of pluripotent cells (FIG. 10B) with a lower proportion of cells in G1 compared to sheep fibroblasts. Also, CTFR-oESC stained positive for pluripotency markers (OCT4 and SOX2) while negative for trophectoderm (CDX2) and primitive endoderm (GATA 4) markers, at both intermediate (p22) and late (P44) passages (FIG. 10C). Finally, positive gene expression of pluripotency markers (OCT4, NANOG, SOX2) and lack of expression of differentiation markers further indicated that CTFR-oESC are pluripotent and stable after prolonged culture (FIG. 10D).

DISCUSSION

Despite years of research, no stable bovine ESC line that can withstand the rigor of extended passaging in culture while maintaining pluripotency has been reported. In the current study, Applicants tested a serum free culture condition (CTFR) for the derivation of bovine ESCs. The results show that CTFR-bESCs are amenable to long-term cultivation and display stable genetic, epigenetic and functional pluripotency features, can be efficiently established by simple whole blastocyst plating of embryos derived from various sources and genetic backgrounds. CTFR-bESCs exhibit molecular features characteristic of primed pluripotency but could integrate into blastocyst ICMs after morula microinjection. In addition, Applicants demonstrated the possibility of using CTFR-bESCs as nuclei donor for the production of NT-cloned embryos.

The culture condition used in this study allows for robust derivation and long-term propagation of pluripotent bESCs. Applicants consider that the combination of factors and specially the addition of a canonical WNT pathway inhibitor (IWR1) were crucial for the derivation of bESCs. IWR1 blocks the translocation of β-catenin to the nucleus by stabilizing AXIN 1/2. The addition of canonical WNT inhibitor has proven effective in deriving and maintaining primed mouse EpiSCs and human ESCs/iPSCs). In the bovine species, maintenance of an inactive canonical WNT-signaling pathway is important for normal pre-implantation and early post-implantation embryo development. Activation of the canonical WNT-β-catenin signaling pathway by the addition of 2-amino-4-(3,4-(methylenedioxy)benzylamino)-6-(3-methoxyphenyl)pyrimidine (AMBMP) during in vitro pre-implantation development has detrimental effects for bovine blastocyst development and reduces the total number of cells in the ICM. Additionally, in vitro treatment of bovine embryos (from day 5 to day 7 after fertilization) with the protein inhibitor of the canonical WNT-signaling pathway (Dickkopf WNT Signaling Pathway Inhibitor 1 (DKK1)), which is naturally secreted by the female reproductive tract and involved in the maternal-to-embryo communication, has shown to significantly improve embryo survival after transfer to recipients. Therefore, it is plausible that the addition of IWR1 was critical for the successful derivation and propagation of bovine ESCs. Indeed, withdrawal of IWR1 from the culture media resulted in loss of pluripotency marker expression. In addition, no bESC lines could be established if IWR1 was not added.

Mouse ESCs are considered as the gold standard for "naïve" PSCs, whose molecular features resemble that of nascent epiblast cells within the ICM. The "primed" state of pluripotency is associated with post-implantation epiblast cells and could be stabilized in cultured mouse EpiSCs. In addition to rodents, naïve-like and primed PSCs have also been described in primate species, including humans, which are mostly defined by respective molecular signatures. All reported naïve-like primate PSCs have not passed the stringent germline chimera assay, and genuine primate naïve PSCs remain elusive. It is possible that species differences may account for the difficulty in obtaining cells equivalent to mouse ESCs in non-rodent species. CTFR-bESCs derived in this study share many defining transcriptional and epigenetic features with mouse EpiSCs and primed human PSCs. For example, the high expression of genes implicated in lineage commitment, e.g. Orthodenticle Homeobox 2 (OTX2) and Zic Family Member 2 (ZIC2), the moderate expression levels of the pluripotency-related transcription factors Homeobox protein NANOG and Kruppel-like factor 4 (KLF4), and the negligible expression of many naïve pluripotency marker genes such as Fibroblast Growth Factor 4 (FGF4), DNA (cytosine-5)-methyltransferase 3-like (DNMT3L), Developmental Pluripotency Associated 2 and 3 (DPPA2 and DPPA3), HORMA domain-containing 1 (HORMAD1), Transcription Factor CP2 Like 1 (TFCP2L1), ZFP42 Zinc Finger Protein (ZFP42 or REX1) and T-Box 3 (TBX3). Epigenetically, primed CTFR-bESCs also shared many features with their mouse and human counterparts, such as the presence of bivalent domains in Homeobox A1 (HOXA1), Forkhead Box A2 (FOXA2), GATA Binding Protein 6 (GATA6), and T-Box 3 (TBX3) genes and the enrichment of H3K27me3-mark in the Homeobox A9 (HOXA9) and NK2 Homeobox 2 (NKX-2) genes.

The ability to generate germline-competent chimeras functionally distinguish naïve mouse ESCs from primed EpiSCs or rsEpiSCs, which are unable to survive in the blastocyst environment and contribute to chimera without genetically enhancing cell survival (e.g. overexpressing anti-apoptotic gene BCL2). Interestingly, it was observed that CTFR-bESCs could survive and colonize the blastocyst ICM after microinjection into morula stage embryos. This is likely, in part, due to superior single cell survival of CTFR-bESCs.

The co-occupancy of H3K4me3- and H3K27me3-marks on gene promoters is one of the most notable epigenetic features of pluripotent cells. These bivalent domains typically localize to key developmental genes that are transcriptionally silenced in ESCs but are poised for activation. Interestingly, 44% of the CTFR-bESC bivalent genes were also present in human and mouse ESCs, suggesting that many molecular features that delineate pluripotency and early lineage commitment are conserved across distant mammalian species. The conserved epigenetic features underlying mammalian pluripotency were further noted in the GO terms for the CTFR-bESC-bivalent genes. Four out of the top-10 enriched GO terms (negative regulation of the canonical Wnt-signaling pathway, neuron migration, central nervous system development, and neuron differentiation) were also found among the top-5 enriched GO terms for bivalent genes in human ESCs according to the database of bivalent genes (BGDB).

The CTFR-bESCs described in this study were: (1) easy to derive from whole blastocysts, (2) fast to obtain, highly efficient to establish, and easy to passage (single cell dissociation using Trypsin). These are desirable characteristics for the creation of genetically superior cattle and the industrial production of valuable pharmaceuticals, as they allow efficient genomic selection through bESC-derivation, facile genome editing, and are amenable for NT-cloning to generate live animals.

In summary, by using a serum-free culture condition, Applicants have derived stable pluripotent bESC lines that can be propagated long-term in culture (more than 70 passages and more than 1 year at the time of writing) while maintaining stable morphology, normal karyotype, pluripotent transcriptome and epigenome signatures, and the ability to generate teratomas containing cells and tissues from three primary germ lineages. Moreover, bESCs could survive and contribute to the ICM of blastocyst embryos after morulas injection, and were successfully used as nuclear donors for cloning. The derivation of stable bESCs opens new avenues for various agricultural and biotechnological applications, e.g. the generation of genetically superior livestock. PSCs have the great potential to be differentiated into any cell type, including gametes. ESCs derived from animals with high genetic value could be differentiated into oocytes and spermatozoa, blastocysts could be produced from these in-vitro-generated gametes, and completion of the life cycle could be achieved by the derivation of superior ESC lines from these blastocysts. This model has been proven already in mice and can be of great use for the generation of genetically superior animals, particularly for species of long generation interval. The condition and protocol developed from this study have worked in cattle and sheep and can potentially be applied to many other ungulate species for the generation of stable ESCs.

Materials and Methods

Embryo Production

In-vitro-matured-in-vitro-fertilized (IVM-IVF) embryos used in this study were produced as previously described by Chitwood et al. (BMC Genomics. 2013 May 25; 14:350. doi: 10.1186/1471-2164-14-350). Ovum pick-up-in-vitro-fertilized (OPU-IVF) and somatic cell nuclear transfer (SCNT)-derived embryos were produced by TansOva Genetics in Sioux Center, IA, using their standard procedures, and shipped overnight to UC Davis for bESC derivation.

Microsurgery and Immunosurgery of Bovine Blastocysts

Isolated ICMs were obtained by microsurgery. Briefly, ZP-depleted blastocysts were placed in a petri dish containing PBS and microsurgery was performed using a micro-blade connected to micromanipulation equipment (Nikon/Narishige, NT88-V3) attached to an inverted microscope (Nikon, TE2000-U).

Immunosurgery was carried out by incubating the embryos in KSOM with 20% anti-horse serum (1 h at 37° C.; Jackson Immunoresearch, West Grove, PA), followed by repeated washes with SOF-HEPES and incubation in KSOM supplemented with 20% guinea pig complement (1 h at 37° C.; Innovative Research, Novi, MI).

Derivation and Culture of CTFR-bESCs

Individual whole blastocysts or isolated ICMs were placed in separate wells of a 12-well dish seeded with a monolayer of gamma-irradiated mouse embryonic fibroblasts (MEF) and cultured in CTFR medium: a custom mTeSR-like basal medium (completely devoid of growth factors FGF2 and TGFβ) containing low fatty acid BSA (MP Biomedicals NZ), similar to basal medium in the published recipe(45) supplemented with 20 ng/ml human FGF2 and 2.5 μM IWR1 (CTFR), and incubated at 37° C. and 5% $CO_2$.

After 48 h, blastocysts/ICMs that failed to adhere to the feeder layer were physically pressed against the bottom of the culture dish with a 22 G needle under a stereoscope to facilitate attachment. Thereafter, the media was changed daily. Outgrowths (after 6-7 days in culture) were dissociated and passaged using TrypLE (Gibco, 12563011) and re-seeded in the presence of Rho Kinase (ROCK) inhibitor (Y-27632, 10 μM) onto newly prepared wells containing MEF and fresh medium (FIG. 1).

Once established, CTFR-bESC lines were grown at 37° C. and 5% $CO_2$ on wells containing MEF and passaged every 4-5 days at a 1:10 split ratio. To increase cell survival, optionally, ROCK inhibitor (Y-27632, 10 μM) was added to the wells 1 h prior to passage and was also added to the newly prepared wells containing MEF and fresh culture media medium during 24 hrs. Media change was done daily between passages. ROCK inhibitor is dispensable for routine maintenance and passaging of CTFR-bESCs.

Immunofluorescense

Cells and embryos were immunostained and imaged as previously described using the following primary antibodies: anti-GATA6 (sc-7244, Santa Cruz Biotechnology, 1:300), anti-SOX2 (ANS79-5M, BioGenex, 1:300), anti-CDX2 (MU392A-UC, BioGenex, 1:300), and anti-OCT4 (sc-8628, Santa Cruz Biotechnology, 1:300).

RNA-Seq

A confluent well of a 6-well plate of CTFR-bESCs grown on MEFs was used per replicate of RNAseq. Total RNA was isolated using Qiagen RNeasy Mini Kit and then reverse-transcribed using iScript RT Supermix (Bio-Rad). Libraries were constructed using the TruSeq RNA Sample Prep Kit (Illumina, San Diego, CA) and sequenced on an Illumina HiSeq 2500 according to the manufacturer's instructions. Sequenced reads were mapped to the bovine UMD3.1 genome assembly and Ensembl 78 genebuild annotation using CLC Genomics Workbench 7.0 (CLCbio, Aarhus, Denmark). Reads per million mapped reads per kilobase of exon model (RPKM) values were calculated for each gene.

ChIP-Seq

CTFR-bESCs were separated from the mouse embryonic fibroblasts using feeder removal microBeads (Miltenyi Biotech, 130-095-531) following the manufacturer's protocol. CTFR-bESCs (20,000 cells) were crosslinked using 0.25% formaldehyde (Pierce, 28906) for 8 min at RT and the crosslinking was stopped by adding 125 mM of Glycine (provided in the True Microchip kit, C01010130). Chromatin immunoprecipitation was performed using the True Micro Chip kit (Diagenode, C01010130) using the following antibodies: anti-H3K27me3 (Millipore, ABE 44) and anti-H3K4me3 (provided with the Diagenode kit). Sequencing libraries were prepared following manufacturer's instructions using the ThruPLEX DNA-seq kit (Rubicon, R400406) with 16 cycles in the library amplification step. Libraries were sequenced at the Vincent J. Coates Genomics Sequencing Laboratory at UC Berkeley in an Illumina HiSeq4000 platform where sequencing was performed as 100 bp paired-end.

Raw Reads were checked for sequencing quality using FastQC and then aligned to the annotated bovine genome (UMD 3.1 assembly) using bwa-aln. Peak calling was done using MACS2(49) with narrow settings for H3K4me3 (-g 2.67e9-q 0.01-m 2 100-B-SPMR) and broad settings for H3K27me3 (-g 2.67e9-q 0.05-m 2 100-broad-B-SPMR-fix-bimodal-extsize 200). Peaks were visualized using golden helix Genome Browser (Bozeman, MT: Golden Helix, Inc. Available from http://www.goldenhelix.com). Called peaks were further analyzed using Hypergeometric Optimization of Motif EnRichment (HOMER) to find peak associations with gene features, and gene ontology analysis was performed using the Database for Annotation, Visualization, and Integrated Discovery (DAVID).

Somatic Cell Nuclear Transfer

For testing the capacity of established CTFR-bESC lines to make NT-blastocysts, several CTFR-bESC lines were used as nuclear donor for reconstructing enucleated oocytes using standard SCNT methodology. Primary fibroblasts were used as controls.

EQUIVALENTS

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

REFERENCES

1. Ying Q L, et al. (2008) The ground state of embryonic stem cell self-renewal. Nature 453(7194):519-523.
2. Wu J & Izpisua Belmonte J C (2015) Dynamic Pluripotent Stem Cell States and Their Applications. Cell Stem Cell 17(5):509-525.
3. Blomberg L A & Telugu B P (2012) Twenty years of embryonic stem cell research in farm animals. Reprod Domest Anim 47 Suppl 4:80-85.
4. Ezashi T, Yuan Y, & Roberts R M (2016) Pluripotent Stem Cells from Domesticated Mammals. Annu Rev Anim Biosci 4:223-253.
5. Soto D A & Ross P J (2016) Pluripotent stem cells and livestock genetic engineering. Transgenic research 25(3): 289-306.
6. Cao S, et al. (2009) Isolation and culture of primary bovine embryonic stem cell colonies by a novel method. J Exp Zool A Ecol Genet Physiol 311(5):368-376.
7. Cibelli J B, et al. (1998) Transgenic bovine chimeric offspring produced from somatic cell-derived stem-like cells. Nat Biotechnol 16(7):642-646.
8. Kim D, Jung Y G, & Roh S (2017) Microarray analysis of embryo-derived bovine pluripotent cells: The vulnerable state of bovine embryonic stem cells. PLoS One 12(3):e0173278.
9. Mitalipova M, Beyhan Z, & First N L (2001) Pluripotency of bovine embryonic cell line derived from precompacting embryos. Cloning 3(2):59-67.
10. Munoz M, et al. (2008) Conventional pluripotency markers are unspecific for bovine embryonic-derived cell-lines. Theriogenology 69(9):1159-1164.
11. Saito S, et al. (2003) Generation of cloned calves and transgenic chimeric embryos from bovine embryonic stem-like cells. Biochem Biophys Res Commun 309(1): 104-113.
12. Saito S, Strelchenko N, & Niemann H (1992) Bovine embryonic stem cell-like cell lines cultured over several passages. Roux Arch Dev Biol 201(3):134-141.
13. Stice S L, Strelchenko N S, Keefer C L, & Matthews L (1996) Pluripotent bovine embryonic cell lines direct embryonic development following nuclear transfer. Biol Reprod 54(1):100-110.
14. Talbot N C, Powell A M, & Rexroad C E, Jr. (1995) In vitro pluripotency of epiblasts derived from bovine blastocysts. Mol Reprod Dev 42(1):35-52.
15. Wang L, et al. (2005) Generation and characterization of pluripotent stem cells from cloned bovine embryos. Biol Reprod 73(1):149-155.
16. Wu X, et al. (2016) Establishment of bovine embryonic stem cells after knockdown of CDX2. Sci Rep 6:28343.
17. De Los Angeles A, et al. (2015) Hallmarks of pluripotency. Nature 525(7570):469-478.

18. Brons I G, et al. (2007) Derivation of pluripotent epiblast stem cells from mammalian embryos. Nature 448(7150): 191-195.

19. Masaki H, et al. (2016) Inhibition of Apoptosis Overcomes Stage-Related Compatibility Barriers to Chimera Formation in Mouse Embryos. Cell Stem Cell 19(5):587-592.

20. Nichols J & Smith A (2009) Naive and primed pluripotent states. Cell Stem Cell 4(6):487-492.

21. Weinberger L, Ayyash M, Novershtern N, & Hanna J H (2016) Dynamic stem cell states: naive to primed pluripotency in rodents and humans. Nat Rev Mol Cell Biol 17(3):155-169.

22. Hanna J, et al. (2010) Human embryonic stem cells with biological and epigenetic characteristics similar to those of mouse ESCs. Proc Natl Acad Sci USA 107(20):9222-9227.

23. Tesar P J, et al. (2007) New cell lines from mouse epiblast share defining features with human embryonic stem cells. Nature 448(7150):196-199.

24. Wu J, et al. (2015) An alternative pluripotent state confers interspecies chimaeric competency. Nature 521 (7552):316-321.

25. Mikkelsen T S, et al. (2007) Genome-wide maps of chromatin state in pluripotent and lineage-committed cells. Nature 448(7153):553-560.

26. Pan G, et al. (2007) Whole-genome analysis of histone H3 lysine 4 and lysine 27 methylation in human embryonic stem cells. Cell Stem Cell 1(3):299-312.

27. Gafni O, et al. (2013) Derivation of novel human ground state naive pluripotent stem cells. Nature 504(7479):282-286.

28. Theunissen T W, et al. (2014) Systematic identification of culture conditions for induction and maintenance of naive human pluripotency. Cell Stem Cell 15(4):471-487.

29. Brook F A & Gardner R L (1997) The origin and efficient derivation of embryonic stem cells in the mouse. Proc Natl Acad Sci USA 94(11):5709-5712.

30. Bryja V, et al. (2006) An efficient method for the derivation of mouse embryonic stem cells. Stem Cells 24(4):844-849.

31. Tian X C, Kubota C, Enright B, & Yang X (2003) Cloning animals by somatic cell nuclear transfer—biological factors. Reprod Biol Endocrinol 1:98.

32. Kim H, et al. (2013) Modulation of beta-catenin function maintains mouse epiblast stem cell and human embryonic stem cell self-renewal. Nat Commun 4:2403.

33. Sugimoto M, et al. (2015) A simple and robust method for establishing homogeneous mouse epiblast stem cell lines by wnt inhibition. Stem Cell Reports 4(4):744-757.

34. Denicol A C, et al. (2014) The WNT signaling antagonist Dickkopf-1 directs lineage commitment and promotes survival of the preimplantation embryo. FASEB J 28(9): 3975-3986.

35. Denicol A C, et al. (2013) Canonical WNT signaling regulates development of bovine embryos to the blastocyst stage. Sci Rep 3:1266.

36. Boroviak T, Loos R, Bertone P, Smith A, & Nichols J (2014) The ability of inner-cell-mass cells to self-renew as embryonic stem cells is acquired following epiblast specification. Nat Cell Biol 16(6):516-528.

37. Buecker C, et al. (2014) Reorganization of enhancer patterns in transition from naive to primed pluripotency. Cell Stem Cell 14(6):838-853.

38. Azuara V, et al. (2006) Chromatin signatures of pluripotent cell lines. Nat Cell Biol 8(5):532-538.

39. Bernstein B E, et al. (2006) A bivalent chromatin structure marks key developmental genes in embryonic stem cells. Cell 125(2):315-326.

40. Sachs M, et al. (2013) Bivalent chromatin marks developmental regulatory genes in the mouse embryonic germline in vivo. Cell Rep 3(6):1777-1784.

41. Sharov A A & Ko M S (2007) Human ES cell profiling broadens the reach of bivalent domains. Cell Stem Cell 1(3):237-238.

42. Tee W W & Reinberg D (2014) Chromatin features and the epigenetic regulation of pluripotency states in ESCs. Development 141(12):2376-2390.

43. Li Q, Lian S, Dai Z, Xiang Q, & Dai X (2013) BGDB: a database of bivalent genes. Database (Oxford) 2013: bat057.

44. Hikabe O, et al. (2016) Reconstitution in vitro of the entire cycle of the mouse female germ line. Nature 539(7628):299-303.

45. Ludwig T E, et al. (2006) Feeder-independent culture of human embryonic stem cells. Nat Methods 3(8):637-646.

46. Ross P J, et al. (2008) Polycomb gene expression and histone H3 lysine 27 trimethylation changes during bovine preimplantation development. Reproduction 136 (6):777-785.

47. Leggett R M, Ramirez-Gonzalez R H, Clavijo B J, Waite D, & Davey R P (2013) Sequencing quality assessment tools to enable data-driven informatics for high throughput genomics. Front Genet 4:288.

48. De Felici M (2009) Primordial germ cell biology at the beginning of the XXI century. The International journal of developmental biology 53(7):891-894.

49. Zhang Y, et al. (2008) Model-based analysis of ChIP-Seq (MACS). Genome Biol 9(9):R137.

50. Heinz S, et al. (2010) Simple combinations of lineage-determining transcription factors prime cis-regulatory elements required for macrophage and B cell identities. Molecular cell 38(4):576-589.

51. Huang da W, Sherman B T, & Lempicki R A (2009) Systematic and integrative analysis of large gene lists using DAVID bioinformatics resources. Nat Protoc 4(1): 44-57.

52. Huang da W, Sherman B T, & Lempicki R A (2009) Bioinformatics enrichment tools: paths toward the comprehensive functional analysis of large gene lists. Nucleic Acids Res 37(1):1-13.

53. Ross P J & Cibelli J B (2010) Bovine somatic cell nuclear transfer. Methods Mol Biol 636:155-177.

54. Canovas S, Cibelli J B, & Ross P J (2012) Jumonji domain-containing protein 3 regulates histone 3 lysine 27 methylation during bovine preimplantation development. Proc Natl Acad Sci USA 109(7):2400-2405.

What is claimed is:

1. A method for culturing pluripotent bovine embryonic stem cells (ESCs), comprising culturing a bovine ESC in the presence of extracellular matrix components produced by Englebreth-Holm-Swarm sarcoma cells or Vitronectin, without inactivated feeder cells, in a cell culture media comprising: (i) an effective amount of Activin-A; (ii) an effective amount of Fibroblast Growth Factor 2 (FGF2); and (i ii) an effective amount of one or more inhibitors of canonical Wnt signaling, thereby preparing cultured bovine ESCs;

wherein the cultured bovine ESCs are stable bovine ESCs that express stable morphology, karyotype and/or pluripotent marker expression and remain stable for at least 34 passages.

2. The method of claim 1, wherein the one or more inhibitors of canonical Wnt signaling are selected from: IWR1, XAV-939, ICG-001, Wnt-C59, LGK-974, LF3, CP21R7, NCB-0846, PNU-74654, Salinomycin, SKL2001, KY02111, IWP-2, IWP-L6, Wnt agonist 1, FH535, WIKI4, PRI-724, IQ-1, KYA1797K, 2,4-diamino-quinazoline, Ant1.4Br, Ant1.4Cl, apicularen, bafilomycin, C59, ETC-159, G007-LK, G244-LM, IWR, Niclosamide, NSC668036, PKF115-584, pyrvinium, Quercetin, Shizokaol D, BC2059, or a combination thereof.

3. The method of claim 1, further comprising isolating the ESCs from the cell culture media.

4. The method of claim 1, further comprising isolating one or more exosomes from the culture media.

5. The method of claim 1, further comprising genetically modifying the bovine ESCs, or the pluripotent cell or the bovine blastocyst cell.

6. The method of claim 1, wherein the bovine embryonic stem cells (ESCs) are isolated from the inner cell mass of blastocyst stage embryos.

7. The method of claim 1, wherein the method further comprises culturing the bovine ESCs for at least 3 weeks.

8. The method of claim 1, wherein the cultured bovine ESCs prepared by the method remain stable for more than 50 passages.

9. The method of claim 1, wherein the cultured bovine ESCs prepared by the method form teratomas in vivo.

\* \* \* \* \*